(12) United States Patent
Liu et al.

(10) Patent No.: US 12,702,772 B2
(45) Date of Patent: Aug. 11, 2026

(54) SYSTEMS AND METHODS OF DETECTING INCORRECT CONNECTIONS IN A HUMIDIFICATION SYSTEM

(71) Applicant: Fisher & Paykel Healthcare Limited, Auckland (NZ)

(72) Inventors: Po-Yen Liu, Auckland (NZ); Ivan Chih-Fan Teng, Auckland (NZ); Ho Shing Lo, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 397 days.

(21) Appl. No.: 18/006,267

(22) PCT Filed: Jul. 28, 2021

(86) PCT No.: PCT/IB2021/056831
§ 371 (c)(1),
(2) Date: Jan. 20, 2023

(87) PCT Pub. No.: WO2022/023984
PCT Pub. Date: Feb. 3, 2022

(65) Prior Publication Data

US 2023/0302240 A1 Sep. 28, 2023

Related U.S. Application Data

(60) Provisional application No. 63/057,731, filed on Jul. 28, 2020.

(51) Int. Cl.
*A61M 16/00* (2006.01)
*A61M 16/08* (2006.01)
(Continued)

(52) U.S. Cl.
CPC ...... *A61M 16/0051* (2013.01); *A61M 16/024* (2017.08); *A61M 16/0883* (2014.02);
(Continued)

(58) Field of Classification Search
None
See application file for complete search history.

(56) References Cited

U.S. PATENT DOCUMENTS 3,806,102 A 4/1974 Valenta et al.
4,778,017 A 10/1988 Liang
(Continued)

FOREIGN PATENT DOCUMENTS

AU 2012216775 3/2014
AU 2010206053 8/2014
(Continued)

OTHER PUBLICATIONS

Search Report in corresponding International Patent Application No. PCT/IB2021/056831, dated Jan. 31, 2023, in 12 pages.
(Continued)

*Primary Examiner* — Reginald S Tillman, Jr.
(74) *Attorney, Agent, or Firm* — Knobbe, Martens, Olson & Bear, LLP

(57) ABSTRACT

Various control methods can indirectly determine incorrect connections between components in a respiratory therapy system. For example, incorrect connections can occur between a patient interface, a humidifier, and/or a gases source. The methods can indirectly detect if reverse flow conditions or other error conditions exist. A reverse flow condition can occur when gases flows in a direction different from an intended direction of flow. The methods can be implemented at the humidifier side, at the gases source side, or both.

20 Claims, 12 Drawing Sheets

(51) Int. Cl.

| | |
|---|---|
| ***A61M 16/10*** | (2006.01) |
| ***A61M 16/16*** | (2006.01) |
| ***G01P 13/00*** | (2006.01) |

(52) U.S. Cl.

CPC ........... *A61M 16/16* (2013.01); *G01P 13/006* (2013.01); *A61M 2016/0033* (2013.01); *A61M 16/1085* (2014.02); *A61M 16/109* (2014.02); *A61M 2205/15* (2013.01); *A61M 2205/3368* (2013.01)

(56) References Cited

U.S. PATENT DOCUMENTS

| | | | |
|---|---|---|---|
| 5,307,243 | A | 4/1994 | Sharp et al. |
| 5,349,946 | A | 9/1994 | McComb |
| 5,359,179 | A | 10/1994 | Desloge et al. |
| 5,367,604 | A | 11/1994 | Murray |
| 5,379,650 | A | 1/1995 | Kofoed et al. |
| 5,782,233 | A | 7/1998 | Niemi et al. |
| 6,039,696 | A | 3/2000 | Bell |
| 6,554,260 | B1 | 4/2003 | Lipscombe et al. |
| 6,983,652 | B2 | 1/2006 | Blakley et al. |
| 7,024,945 | B2 | 4/2006 | Wallace |
| 7,093,501 | B2 | 8/2006 | Kuo et al. |
| 7,525,663 | B2 | 4/2009 | Kwok et al. |
| 8,049,143 | B2 | 11/2011 | Andel et al. |
| 8,063,343 | B2 | 11/2011 | Mcghin et al. |
| 8,381,729 | B2 | 2/2013 | Freitag et al. |
| 8,733,349 | B2 | 5/2014 | Bath et al. |
| 9,937,314 | B2 | 4/2018 | Buechi et al. |
| 9,937,316 | B2 | 4/2018 | Buechi et al. |
| 9,943,108 | B2 | 4/2018 | Lord |
| 10,398,871 | B2 | 9/2019 | Cortez, Jr. et al. |
| 11,684,736 | B2 | 6/2023 | Liu et al. |
| 2002/0100320 | A1 | 8/2002 | Smith et al. |
| 2003/0116556 | A1 | 6/2003 | Li |
| 2006/0211981 | A1 | 9/2006 | Sparks et al. |
| 2007/0181127 | A1 | 8/2007 | Jin et al. |
| 2007/0265877 | A1 | 11/2007 | Rice et al. |
| 2007/0272239 | A1 | 11/2007 | Aylsworth et al. |
| 2008/0308100 | A1 | 12/2008 | Pujol et al. |
| 2009/0045829 | A1 | 2/2009 | Awazu et al. |
| 2009/0110379 | A1 | 4/2009 | Mcghin et al. |
| 2009/0194106 | A1 | 8/2009 | Smith et al. |
| 2010/0206308 | A1 | 8/2010 | Klasek et al. |
| 2011/0023874 | A1 | 2/2011 | Bath et al. |
| 2011/0049123 | A1 | 3/2011 | Frock et al. |
| 2011/0088693 | A1 | 4/2011 | Somervell et al. |
| 2011/0162647 | A1 | 7/2011 | Huby et al. |
| 2011/0253136 | A1 | 10/2011 | Sweeney et al. |
| 2012/0017904 | A1 | 1/2012 | Ratto et al. |
| 2012/0073573 | A1 | 3/2012 | Thudor et al. |
| 2012/0125333 | A1 | 5/2012 | Bedford et al. |
| 2012/0248636 | A1 | 10/2012 | Fridberg et al. |
| 2013/0081621 | A1 | 4/2013 | Korneff et al. |
| 2014/0202460 | A1 | 7/2014 | Bath et al. |
| 2014/0216459 | A1 | 8/2014 | Vos et al. |
| 2014/0238394 | A1 | 8/2014 | Beuchi |
| 2014/0261418 | A1 | 9/2014 | Huang |
| 2015/0048530 | A1 | 2/2015 | Cheung et al. |
| 2015/0273175 | A1 | 10/2015 | Acker et al. |
| 2017/0266399 | A1 | 9/2017 | Campana et al. |
| 2018/0028773 | A1 | 2/2018 | Klasek et al. |
| 2018/0236191 | A1 | 8/2018 | Martin |
| 2020/0206442 | A1 | 7/2020 | Knepper et al. |
| 2022/0160977 | A1 | 5/2022 | Teng et al. |
| 2023/0310779 | A1 | 10/2023 | Liu et al. |

FOREIGN PATENT DOCUMENTS

| | | | |
|---|---|---|---|
| AU | 2017268523 | A1 | 12/2017 |
| CN | 205227470 | U | 5/2016 |
| EP | 1 014 527 | A2 | 6/2000 |
| EP | 2 039 387 | A1 | 3/2009 |
| EP | 2 143 459 | | 1/2010 |
| EP | 2 229 973 | | 9/2010 |
| EP | 2 524 714 | | 11/2012 |
| EP | 3 139 986 | | 3/2017 |
| GB | 2495771 | | 7/2018 |
| JP | H9-70437 | A | 3/1997 |
| JP | 2016-118511 | A | 6/2016 |
| JP | 2017-153289 | | 8/2017 |
| NZ | 5 87113 | A | 12/2011 |
| WO | WO 2000/027457 | | 5/2000 |
| WO | WO 2003/048721 | | 6/2003 |
| WO | WO 2006/092001 | | 9/2006 |
| WO | WO 2008/055307 | | 5/2008 |
| WO | WO 2008/091164 | | 7/2008 |
| WO | WO 2009/085995 | | 7/2009 |
| WO | WO 2010/031126 | | 3/2010 |
| WO | WO 2010/141983 | | 12/2010 |
| WO | WO 2012/080941 | | 6/2012 |
| WO | WO 2012/135912 | | 10/2012 |
| WO | WO 2012/164407 | | 12/2012 |
| WO | WO 2013/057146 | | 4/2013 |
| WO | WO 2013/147623 | | 10/2013 |
| WO | WO 2013/165263 | | 11/2013 |
| WO | WO 2013/176557 | | 11/2013 |
| WO | WO 2014/052983 | | 4/2014 |
| WO | WO 2015/038014 | A1 | 3/2015 |
| WO | WO 2015/135040 | | 9/2015 |
| WO | WO 2017/027906 | | 2/2017 |
| WO | WO 2017/126980 | A2 | 7/2017 |
| WO | WO 2018/070883 | A1 | 4/2018 |
| WO | WO 2020/204731 | | 10/2020 |
| WO | WO 2022/023984 | A1 | 2/2022 |

OTHER PUBLICATIONS

Written Opinion in corresponding International Patent Application No. PCT/IB2021/056831, dated Nov. 1, 2021, in 11 pages.

International Preliminary Report on Patentability in corresponding International Patent Application No. PCT/IB2021/056831, dated Jan. 31, 2023, in 12 pages.

SYSTEMS AND METHODS OF DETECTING INCORRECT CONNECTIONS IN A HUMIDIFICATION SYSTEM

FIELD

The present application relates to a humidification system for providing humidified gases to a user or a patient. In particular, the present application relates to detecting connection errors and/or a condition indicative of connection errors between components in the humidification system.

BACKGROUND

A number of methods can be used to supply humidified gases to a user or a patient. Respiratory assistance humidification systems generally include a source of pressurized gases (for example, air, oxygen or other mixtures of gases) such as a ventilator, a humidifier including a source of water and a heat source to vaporize the water so as to humidify the gases from the gases source, and an inspiratory conduit to convey the humidified gases to a patient interface, such as a mask, a nasal cannula, and the like. Humidification systems can be single-limb or dual-limb. In a single-limb system, exhaled gases from the patient can be released into the ambient air via vent holes on the patient interface or some other venting device. In a dual-limb system, exhaled gases can be conveyed from the patient back to the gases source via an expiratory conduit.

SUMMARY

For proper functioning of a humidification system the gases flow should flow in a normal (that is, correct or operative or therapeutic) direction from the gases source through the humidifier to the patient and that the components of the humidification system are connected correctly in order to facilitate gases flow in the normal direction (that is, correct or operative or therapeutic direction). The correct or normal direction can be termed as a forward flow direction. The correct connections and normal flow direction can ensure that the gases are delivered to the patient at a desired humidity and a desired temperature. The desired humidity is a therapeutic humidity level. Incorrect connections in the humidification system can occur between various components, for example, between two or more of the patient interface, conduits that transport gases, humidifier and/or to/from gases source.

Incorrect connections in the humidification system (which can include at least a gases source, a dry line, a humidifier, an inspiratory conduit, a patient interface, an expiratory conduit, and any connectors therebetween) can be due to a set up error. The gases source can include one or more sources of respiratory gases, which will be shorted to "gases source" throughout this disclosure. Caregivers can incorrectly couple conduits that have the corresponding end connectors of the same type, such as the 22 mm male and female medical taper connectors or other standard connectors. The caregiver can connect the humidifier and gases source incorrectly (for example, such that the gas does not flow from the gases source to the humidifier). Non-standard connections may help ameliorate this issue, such as, for example, at the humidifier outlet, on the inlet and outlet of the gases source or on a conduit. However, this can cause manufacturing complexities and increase costs, and/or may be confusing for the caregiver or user. Moreover, some connections may be standardized connectors required by regulations and/or by commercial necessity, which may not be feasibly changed to a non-standard connector. Other components of the humidification system can also be incorrectly connected to each other.

The incorrect connections can result in reverse flow conditions. A reverse flow condition can be a condition when the gases flow in the wrong (that is, incorrect or reverse) direction as compared to a forward flow direction (that is, desired or therapeutic or normal direction). A reverse flow condition is a condition when gases flow in an opposite direction to the forward flow direction. Reverse flow condition can also include gases flowing in an incorrect direction (that is, not in the forward flow direction). Incorrect connections of the components can result in the gases being delivered to the patient outside therapeutic humidity ranges and/or outside desired temperature or therapeutic temperature ranges. This can lead to unsatisfactory treatments, discomfort, and/or adverse reactions in the patient. For example, dry air can be delivered from the gases source directly to the patient, whereas humidified gases can be delivered to the gases source. In this regard, such incorrect configuration can result in the humidifier being bypassed, resulting in dry gas being delivered to the patient. Dry gases can cause discomfort and/or may also cause damage to the patient's airways. In some examples, incorrect connections can cause exhaled air from the patient to be delivered to the humidifier. In a reverse flow condition, damage can also occur to the gases source (for example, the ventilator or other gases source) due to provision of humidity to the gases source. The humidity provided to the gases source can cause condensate formation that can damage the gases source.

A reverse flow condition can be indicative of incorrect connections or an incorrect set up by a clinician or nurse. Humidification systems of the present disclosure can automatically detect incorrect connections and alert a user. The system can detect errors in the connections between components such as for between patient interface, humidifier, and/or gases source, in the system. Humidification systems of the present disclosure can detect incorrect conduit connection within the system. Humidification systems of the present disclosure can detect the existence of a reverse flow condition/situation (that is, a condition where gases are flowing in the wrong direction) where a patient is receiving sub-optimal humidity and/or temperature. The methods disclosed herein can detect if the gases are flowing in the wrong direction. The wrong direction is a reverse flow direction. A reverse flow condition detected by the methods described herein likely indicates errors in the connections between two or more components of the humidification system. The incorrect connection can include improper connection and/or disconnection of the expiratory conduit. The reverse flow condition detection can include warning a user. The disclosed methods may also determine a fault or an incorrect operation parameter detected in the system, which is indicative of incorrect connections in the system (that is, incorrect connections between components in the system).

The present disclosure also relates to detection of incorrect connection of the expiratory conduit in dual-limb systems, such as systems used for providing invasive mechanical ventilation therapies, noninvasive mechanical ventilation therapies, neonatal invasive or noninvasive therapies and/or other therapies.

In some configurations, the present disclosure provides a method of detecting reverse flow condition in a respiratory humidification system including a gases source, a controller, a humidifier, and a breathing circuit. The method can include using the controller of the humidification system: measuring an outlet temperature using a sensor at or near an outlet of a chamber of the humidifier; and in response to detecting at least two trigger events, outputting an indication of a reverse flow condition, wherein a trigger event can comprise the chamber outlet temperature reaching a first threshold temperature.

In some configurations, outputting the indication of the reverse flow condition can be further in response to detecting a pattern of the at least two trigger events.

In some configurations, the method can further comprise starting or restarting a timer in response to detecting a first one of the at least two trigger events.

In some configurations, in response to restarting the timer, the method can further comprise restarting the timer from a time when a trigger event was most recently detected.

In some configurations, the timer can expire after between 5 minute and 120 minutes.

In some configurations, the timer can expire after between 5 minute and 60 minutes.

In some configurations, the timer can expire after between 5 minute and 30 minutes.

In some configurations, the timer can expire after between 5 minute and 20 minutes.

In some configurations, the timer can expire after between 5 minute and 10 minutes.

In some configurations, the method can further comprise determining whether the timer has expired in response to no trigger event being detected.

In some configurations, the method can further comprise incrementing a counter in response to starting or restarting the timer.

In some configurations, incrementing the counter can comprise incrementing the counter by a value of 1.

In some configurations, the pattern can comprise the counter having a value that is greater than or equal to a counter threshold.

In some configurations, the counter threshold can be between 2 to 20 times.

In some configurations, the counter threshold can be between 5 to 15 times.

In some configurations, the counter threshold can be between 5 to 10 times.

In some configurations, the method can further comprise clearing or resetting the outputted indication of the reverse flow condition in response to the counter having a value that is below the counter threshold.

In some configurations, the method can further comprise resetting the counter in response to a determination that the timer has expired.

In some configurations, the method can further comprise initiating a second method of detecting an indication of a reverse flow condition in response to outputting the indication of the reverse flow condition.

In some configurations, the method can further comprise disabling power to a heater plate of the humidifier and/or a heat source in an inspiratory conduit of the breathing circuit in response to outputting the indication of the reverse flow condition.

In some configurations, disabling power to the heater plate of the humidifier and/or the heat source in the inspiratory conduit can comprise using a safety feature.

In some configurations, the safety feature can comprise a hardware component.

In some configurations, the hardware component can comprise a thermal cut-out.

In some configurations, the hardware component can comprise one or more switches.

In some configurations, the switch can comprise a relay.

In some configurations, the switch can comprise a transistor.

In some configurations, the safety feature can be electrically coupled with the controller or a different microcontroller.

In some configurations, outputting the indication of the reverse flow condition further can comprise activating an alarm.

In some configurations, the alarm can be visual and/or audible.

In some configurations, the method can further comprise causing the alarm to be displayed on a user interface of the humidifier and/or the gases source.

In some configurations, the alarm can be activated only after a pre-determined operating time period has been reached.

In some configurations, the first threshold temperature can comprise a chamber outlet cut-out temperature.

In some configurations, the first threshold temperature can be above 37° C.

In some configurations, the first threshold temperature can be between 37.1° C. and 50° C.

In some configurations, the first threshold temperature can be between 38° C. and 45° C.

In some configurations, the first threshold temperature can be between 42° C. and 44° C.

In some configurations, in response to detecting a first one of the at least two trigger events, the method further comprise detecting a subsequent one of the at least two trigger events only after the chamber outlet temperature has fallen below a second threshold temperature.

In some configurations, detecting the first one or the subsequent one of the at least two trigger events can comprise incrementing a counter.

In some configurations, the second threshold temperature can be below the first threshold temperature and above a chamber outlet temperature setpoint.

In some configurations, detecting the subsequent one of the at least two trigger events only after the chamber outlet temperature has fallen below the second threshold temperature can be configured to provide hysteresis.

In some configurations, the method can be performed during setup of the system or just after setup is finished.

In some configurations, the method can be performed during steady state operation of the system.

In some configurations, the method can be performed by interrupting steady state operation for a period of time.

In some configurations, detecting the pattern can be based on a predetermined periodicity of the at least two trigger events.

In some configurations, detecting the pattern can comprise using one or more of Fast Fourier Transform, autocorrelation, and/or statistical analysis.

In some configurations, detecting the pattern can comprise using a sliding window.

In some configurations, the present disclosure can include a reverse flow detector for a humidification system that includes a gases source, a humidifier, and a breathing circuit, and configured to detect a reverse flow condition in the humidification system. The detector can comprise a controller configured to: receive a sensor signal indicative of an outlet temperature at an outlet of a chamber of the humidifier that carries humidification fluid; and in response to in response to detecting at least two trigger events, output an indication of a reverse flow condition, wherein a trigger event can comprise the chamber outlet temperature reaching a first threshold temperature.

In some configurations, the controller can be configured to output the indication of the reverse flow condition further in response to detecting a pattern of the at least two trigger events.

In some configurations, the controller can be further configured to start or restart a timer in response to detecting a first one of the at least two trigger event.

In some configurations, the controller can be configured to restart the timer from a time when a trigger event was most recently detected.

In some configurations, the timer can expire after between 5 minute and 120 minutes.

In some configurations, the timer can expire after between 5 minute and 60 minutes.

In some configurations, the timer can expire after between 5 minute and 30 minutes.

In some configurations, the timer can expire after between 5 minute and 20 minutes.

In some configurations, the timer can expire after between 5 minute and 10 minutes.

In some configurations, the controller can be further configured to determine whether the timer has expired in response to no trigger event being detected.

In some configurations, the controller can be further configured to increment a counter in response to starting or restarting the timer.

In some configurations, the controller can be configured to increment the counter by a value of 1.

In some configurations, the pattern can comprise the counter having a value that is greater than or equal to a counter threshold.

In some configurations, the counter threshold can be between 2 to 20 times.

In some configurations, the counter threshold can be between 5 to 15 times.

In some configurations, the counter threshold can be between 5 to 10 times.

In some configurations, the controller can be further configured to clear or reset the outputted indication of the reverse flow condition in response to the counter having a value that is below the counter threshold.

In some configurations, the controller can be further configured to reset the counter in response to a determination that the timer has expired.

In some configurations, the controller can be further configured to initiate a second method of detecting an indication of a reverse flow condition in response to outputting the indication of the reverse flow condition.

In some configurations, the controller can be configured to output the indication of the reverse flow condition by activating an alarm.

In some configurations, the alarm can be visual and/or audible.

In some configurations, the controller can be further configured to cause the alarm to be displayed on a user interface of the humidifier and/or the gases source.

In some configurations, the alarm can be activated only after a pre-determined operating time period has been reached.

In some configurations, the first threshold temperature can comprise a chamber outlet cut-out temperature.

In some configurations, the first threshold temperature can be above 37° C.

In some configurations, the first threshold temperature can be between 37.1° C. and 50° C.

In some configurations, the first threshold temperature can be between 38° C. and 45° C.

In some configurations, the first threshold temperature can be between 42° C. and 44° C.

In some configurations, in response to detecting a first one of the at least two trigger events, the controller can be further configured to detect a subsequent one of the at least two trigger events only after the chamber outlet temperature has fallen below a second threshold temperature.

In some configurations, the controller can be configured to detect the first one or the subsequent one of the at least two trigger events by incrementing a counter.

In some configurations, the second threshold temperature can be below the first threshold temperature and above a chamber outlet temperature setpoint.

In some configurations, the controller can be configured to detect the subsequent one of the at least two trigger events only after the chamber outlet temperature has fallen below the second threshold temperature to prevent hysteresis.

In some configurations, the detecting can be performed during setup of the system or just after setup is finished.

In some configurations, the detecting can be performed during steady state operation of the system.

In some configurations, the detecting can be performed by interrupting steady state operation for a period of time.

In some configurations, the controller can be configured to detect the pattern based on a predetermined periodicity of the at least two trigger events.

In some configurations, the controller can be configured to detect the pattern comprises using one or more of Fast Fourier Transform, autocorrelation, and/or statistical analysis.

In some configurations, the controller can be configured to detect the pattern using a sliding window.

In some configurations, a humidifier for a humidification system can comprise any configurations of the reverse flow detector described above.

In some configurations, the controller can be further configured to disable power to a heater plate of the humidifier and/or a heat source in an inspiratory conduit of the breathing circuit in response to outputting the indication of the reverse flow condition.

In some configurations, the humidifier can further comprise a safety feature configured to disable power to the heater plate of the humidifier and/or the heat source in the inspiratory conduit in response to outputting the indication of the reverse flow condition.

In some configurations, the safety feature can comprise a hardware component.

In some configurations, the hardware component can comprise a thermal cut-out.

In some configurations, the hardware component can comprise one or more switches.

In some configurations, the switch can comprise a relay.

In some configurations, the switch can comprise a transistor.

In some configurations, the safety feature can be electrically coupled with the controller or a different microcontroller.

In some configurations, a humidification system can comprise a gases source, a humidifier, and a breathing circuit, wherein the gases source can comprise any configurations of the reverse flow detector described above.

In some configurations, the present disclosure provides a method of detecting reverse flow in a respiratory humidification system including a gases source, a controller, a humidifier including an inlet and an outlet, and an inspiratory conduit. The method can comprise using the controller of the humidification system: determining a first patient end temperature at or near a patient end of the inspiratory conduit and/or a first outlet temperature at or near the outlet of the humidifier; providing an electrical power to an inspiratory conduit heat source in the inspiratory conduit; determining a second patient end temperature at or near the patient end of the inspiratory conduit and a second outlet temperature at or near the outlet of the humidifier after providing the electrical power to the inspiratory conduit heat source; comparing the first patient end temperature with the second patient end temperature and/or comparing the first outlet temperature with the second outlet temperature;

in response to the second patient end temperature being greater than the first patient end temperature and/or the second outlet temperature being greater than the first outlet temperature, comparing at least one of: the second patient end temperature with the second outlet temperature, a change in the second patient end temperature with a change in the second outlet temperature over a predetermined time period, and/or a rate of change in the second patient end temperature with a rate of change in the second outlet temperature over the predetermined time period; and outputting an indication of reverse flow conditions in response to at least one of: the second patient end temperature being lower than the second outlet temperature, the change in the second patient end temperature being lower than the change in the second outlet temperature over the predetermined time period, and/or the rate of change in the second patient end temperature being lower than the rate of change in the second outlet temperature over the predetermined time period.

In some configurations, the method can further comprise executing a first timeout reset function in response to the method having not been started at an end of a first timeout period.

In some configurations, the method can further comprise proceeding to therapy operation upon executing the first timeout reset function.

In some configurations, the method can further comprise detecting a minimum flow rate of a gases flow in the system prior to determining the first patient end temperature and the first outlet temperature.

In some configurations, the minimum flow rate can be a filtered flow rate.

In some configurations, the minimum flow rate can be about 3 L/min.

In some configurations, the method can further comprise executing a first timeout reset function in response to the gases flow having a flow rate below the minimum flow rate.

In some configurations, the electrical power to the inspiratory conduit heat source can be a maximum electrical power.

In some configurations, the method can further comprise disabling electrical power to a heater plate of the humidifier.

In some configurations, the method can further comprise reducing electrical power to a heater plate of the humidifier to at or below 20% of a duty cycle.

In some configurations, the method can further comprise providing the electrical power to the inspiratory conduit heat source until the second patient end temperature is greater than the first patient end temperature and/or the second outlet temperature is greater than the first outlet temperature.

In some configurations, the method can further comprise executing a second timeout reset function in response to the controller providing the electrical power to the inspiratory conduit heat source at an end of a second timeout period.

In some configurations, the method can further comprise proceeding to therapy operation upon executing the second timeout reset function.

In some configurations, the comparing can be in response to the second patient end temperature being greater than the first patient end temperature by a first offset value and/or the second outlet temperature being greater than the first outlet temperature by a second offset value.

In some configurations, the first and/or second offset values can be up to about 5° C.

In some configurations, the first and/or second offset values can be between about 1.5° C. and about 5° C.

In some configurations, the first and/or second offset values can be about 2° C.

In some configurations, the method can be performed during setup of the system.

In some configurations, the setup can further comprise a water-out detection test in response to no reverse flow condition being detected.

In some configurations, the method can be performed during therapy operation of the system.

In some configurations, the method can further comprise resume therapy operation after outputting the indication of reverse flow condition.

In some configurations, the indication can comprise a reverse flow alarm.

In some configurations, the present disclosure provides a method of detecting reverse flow in a respiratory humidification system including a gases source, a controller, a humidifier including an inlet and an outlet, and an inspiratory conduit. The method can comprise using the controller of the humidification system: providing an electrical power to an inspiratory conduit heat source in the inspiratory conduit for a predetermined period of time; determining a patient end temperature at or near a patient end of the inspiratory conduit and a chamber outlet temperature at or near the outlet of the humidifier after providing the electrical power to the inspiratory conduit heat source for the predetermined period of time; and outputting an indication of reverse flow conditions in response to at least one of: the patient end temperature being lower than the outlet temperature, the change in the patient end temperature being lower than the change in the outlet temperature over the predetermined time period, and/or the rate of change in the patient end temperature being lower than the rate of change in the outlet temperature over the predetermined time period.

In some configurations, the method can further comprise executing a timeout reset function in response to the method having not been started at an end of a timeout period.

In some configurations, the method can further comprise proceeding to therapy operation upon executing the timeout reset function.

In some configurations, the method can further comprise detecting a minimum flow rate of a gases flow in the system prior to determining the first patient end temperature and the first outlet temperature.

In some configurations, the minimum flow rate can be a filtered flow rate.

In some configurations, the minimum flow rate can be about 3 L/min.

In some configurations, the method can further comprise executing a timeout reset function in response to the gases flow having a flow rate below the minimum flow rate.

In some configurations, the electrical power to the inspiratory conduit heat source can be a maximum electrical power.

In some configurations, the method can further comprise disabling electrical power to a heater plate of the humidifier.

In some configurations, the method can further comprise reducing electrical power to a heater plate of the humidifier to at or below 20% of a duty cycle.

In some configurations, the method can further comprise comparing the patient end temperature with a baseline patient end temperature, and/or comparing the outlet temperature with a baseline outlet temperature, after providing an electrical power to the inspiratory conduit heat source in the inspiratory conduit for the predetermined period of time, wherein the baseline outlet temperature and/or the baseline patient end temperature can be measured before providing an electrical power to the inspiratory conduit heat source.

In some configurations, the electrical power can be provided to the inspiratory conduit heat source until the second patient end temperature is greater than the first patient end temperature and/or the second outlet temperature is greater than the first outlet temperature.

In some configurations, the comparing can be in response to the second patient end temperature being greater than the first patient end temperature by a first offset value and/or the second outlet temperature being greater than the first outlet temperature by a second offset value.

In some configurations, the first and/or second offset values can be up to about 5° C.

In some configurations, the first and/or second offset values can be between about 1.5° C. and about 5° C.

In some configurations, the first and/or second offset values can be about 2° C.

In some configurations, the method can be performed during setup of the system.

In some configurations, the setup can further comprise a water-out detection test in response to no reverse flow condition being detected.

In some configurations, the method can be performed during therapy operation of the system.

In some configurations, the method can further comprise resume therapy operation after outputting the indication of reverse flow condition.

In some configurations, the indication can comprise a reverse flow alarm.

In some configurations, the present disclosure presents a reverse flow detector of a respiratory humidification system. The detector can comprise a controller configured to be in electrical communication with a first sensor and a second sensor, wherein the first sensor is at or near a patient end of an inspiratory conduit and configured to measure a patient end temperature, and the second sensor is at or near an outlet of a humidifier and configured to measure an outlet temperature, the inspiratory conduit configured to provide humidified gases to a user and including an inspiratory conduit heat source, the humidifier configured to humidify gases and further including a humidifier heat source to heat a liquid to humidify the gases provided by a gases source; the controller configured to detect an indication of reverse flow conditions in the humidification system by being configured to: determine a first patient end temperature at a patient end of the inspiratory conduit and/or a first outlet temperature at the outlet of the humidifier; provide an electrical power to the inspiratory conduit heat source; determine a second patient end temperature and a second outlet temperature after providing the electrical power to the inspiratory conduit heat source; compare the first patient end temperature with the second patient end temperature and/or compare the first outlet temperature with the second outlet temperature; in response to the second patient end temperature being greater than the first patient end temperature and/or the second outlet temperature being greater than the first outlet temperature, compare at least one of: the second patient end temperature with the second outlet temperature, a change in the second patient end temperature with a change in the second outlet temperature over a predetermined time period, and/or a rate of change in the second patient end temperature with a rate of change in the second outlet temperature over the predetermined time period; and output an indication of reverse flow conditions in response to at least one of: the second patient end temperature being lower than the second outlet temperature, the change in the second patient end temperature being lower than the change in the second outlet temperature over the predetermined time period, and/or the rate of change in the second patient end temperature being lower than the rate of change in the second outlet temperature over the predetermined time period.

In some configurations, the controller can be further configured to execute a timeout reset function in response to the method having not been started at an end of a timeout period.

In some configurations, the controller can be further configured to proceed to therapy operation upon executing the timeout reset function.

In some configurations, the controller can be further configured to detect a minimum flow rate of a gases flow in the system prior to determining the first patient end temperature and the first outlet temperature.

In some configurations, the minimum flow rate can be a filtered flow rate.

In some configurations, the minimum flow rate can be about 3 L/min.

In some configurations, the controller can be further configured to execute a timeout reset function in response to the gases flow having a flow rate below the minimum flow rate.

In some configurations, the electrical power to the inspiratory conduit heat source can be a maximum electrical power.

In some configurations, the controller can be further configured to disable electrical power to a heater plate of the humidifier (optionally in response to detection of reverse flow).

In some configurations, the controller can be further configured to reduce electrical power to a heater plate of the humidifier to at or below 20% of a duty cycle (optionally in response to detection of reverse flow).

In some configurations, the controller can be further configured to provide the electrical power to the inspiratory conduit heat source until the second patient end temperature is greater than the first patient end temperature and/or the second outlet temperature is greater than the first outlet temperature.

In some configurations, the controller can be further configured to execute a second timeout reset function in response to the controller providing the electrical power to the inspiratory conduit heat source at an end of a second timeout period.

In some configurations, the controller can be further configured to proceed to therapy operation upon executing the second timeout reset function.

In some configurations, the comparing can be in response to the second patient end temperature being greater than the first patient end temperature by a first offset value and/or the second outlet temperature being greater than the first outlet temperature by a second offset value.

In some configurations, the first and/or second offset values can be up to about 5° C.

In some configurations, the first and/or second offset values can be between about 1.5° C. and about 5° C.

In some configurations, the first and/or second offset values can be about 2° C.

In some configurations, the controller can be configured to perform the reverse flow detection during setup of the system.

In some configurations, the setup can further comprise a water-out detection test in response to no reverse flow condition being detected.

In some configurations, the controller can be configured to perform the reverse flow detection during therapy operation of the system.

In some configurations, the controller can be further configured to resume therapy operation after outputting the indication of reverse flow condition.

In some configurations, the indication can comprise a reverse flow alarm.

In some configurations, a humidifier for a humidification system can comprise any configurations of the reverse flow detector described above.

In some configurations, a humidification system can comprise a gases source, a humidifier, and a breathing circuit, wherein the gases source can comprise any configurations of the reverse flow detector described above.

In some configurations, the present disclosure presents a reverse flow detector of a respiratory humidification system. The detector can comprise a controller configured to be in electrical communication with a first sensor and a second sensor, wherein the first sensor is at or near a patient end of an inspiratory conduit and configured to measure a patient end temperature, and the second sensor is at or near an outlet of a humidifier and configured to measure an outlet temperature, the inspiratory conduit configured to provide humidified gases to a user and including an inspiratory conduit heat source, the humidifier configured to humidify gases and further including a humidifier heat source to heat a liquid to humidify the gases provided by a gases source; the controller configured to detect an indication of reverse flow conditions in the humidification system by being configured to: provide an electrical power to an inspiratory conduit heat source in the inspiratory conduit for a predetermined period of time; determine a patient end temperature at or near a patient end of the inspiratory conduit and a chamber outlet temperature at or near the outlet of the humidifier after providing the electrical power to the inspiratory conduit heat source for the predetermined period of time; and output an indication of reverse flow conditions in response to at least one of: the patient end temperature being lower than the outlet temperature, the change in the patient end temperature being lower than the change in the outlet temperature over the predetermined time period, and/or the rate of change in the patient end temperature being lower than the rate of change in the outlet temperature over the predetermined time period.

In some configurations, the controller can be further configured to execute a first timeout reset function in response to the method having not been started at an end of a first timeout period.

In some configurations, the controller can be further configured to proceed to therapy operation upon executing the timeout reset function.

In some configurations, the controller can be further configured to detect a minimum flow rate of a gases flow in the system prior to determining the first patient end temperature and the first outlet temperature.

In some configurations, the minimum flow rate can be a filtered flow rate.

In some configurations, the minimum flow rate can be about 3 L/min.

In some configurations, the controller can be further configured to execute a timeout reset function in response to the gases flow having a flow rate below the minimum flow rate.

In some configurations, the electrical power to the inspiratory conduit heat source can be a maximum electrical power.

In some configurations, the controller can be further configured to disable electrical power to a heater plate of the humidifier (optionally in response to detection of reverse flow).

In some configurations, the controller can be further configured to reduce electrical power to a heater plate of the humidifier to at or below 20% of a duty cycle (optionally in response to detection of reverse flow).

In some configurations, the controller can be further configured to compare the patient end temperature with a baseline patient end temperature, and/or comparing the outlet temperature with a baseline outlet temperature, after providing an electrical power to the inspiratory conduit heat source in the inspiratory conduit for the predetermined period of time, wherein the baseline outlet temperature and/or the baseline patient end temperature were measured before providing an electrical power to the inspiratory conduit heat source.

In some configurations, the controller can be configured to provide the electrical power to the inspiratory conduit heat source until the second patient end temperature is greater than the first patient end temperature and/or the second outlet temperature is greater than the first outlet temperature.

In some configurations, the controller can be configured to compare the patient end temperature with the baseline patient end temperature plus a first offset value and/or the outlet temperature with the baseline outlet temperature plus a second offset value.

In some configurations, the first and/or second offset values can be up to about 5° C.

In some configurations, the first and/or second offset values can be between about 1.5° C. and about 5° C.

In some configurations, the first and/or second offset values can be about 2° C.

In some configurations, the controller can be configured to perform the reverse flow detection during setup of the system.

In some configurations, the setup can further comprise a water-out detection test in response to no reverse flow condition being detected.

In some configurations, the controller can be configured to perform the reverse flow detection during therapy operation of the system.

In some configurations, the controller can be further configured to resume therapy operation after outputting the indication of reverse flow condition.

In some configurations, the indication can comprise a reverse flow alarm.

In some configurations, a humidifier for a humidification system can comprise any configurations of the reverse flow detector described above.

In some configurations, a humidification system can comprise a gases source, a humidifier, and a breathing circuit, wherein the gases source can comprise any configurations of the reverse flow detector described above.

In some configurations, the present disclosure provides a method of detecting reverse flow in a respiratory humidification system including a gases source, a humidifier including an inlet and an outlet, an inspiratory conduit, and a plurality of sensors. The method can comprise using a controller of the system: receiving inputs from one or more of the plurality of sensors; determining that the inputs are at steady state; calculating a reverse flow indicator based at least in part on at least some of the inputs; and outputting an indication of a reverse flow condition in response to the reverse flow indicator exceeding a threshold.

In some configurations, the inputs can be determined to be at steady state for a predetermined period of time.

In some configurations, the steady state of the inputs can comprise a rate of change of the inputs under a fluctuation limit for the predetermined period of time.

In some configurations, the method can further comprise executing a reset function in response to predetermined system conditions.

In some configurations, the method can further comprise determining a humidifier outlet state based on whether a temperature at the humidifier outlet has reached a pre-set limit.

In some configurations, calculating the indication of the reverse flow condition can comprise using different equations depending on the determined humidifier outlet state.

In some configurations, the different equations can comprise at least one coefficient that is different in the equations.

In some configurations, the method can further comprise ignoring at least readings from a sensor configured to measure the temperature of the humidifier outlet in response to the determined humidifier outlet state.

In some configurations, the method can further comprise updating a confidence counter, wherein the counter can be incremented in response to the inputs being at steady state for the predetermined period of time.

In some configurations, the calculating the reverse flow indicator can be performed in response to the confidence counter reaching a minimum count.

In some configurations, the updating the confidence counter can be performed after the calculating the reverse flow indicator.

In some configurations, the method can further comprise setting a reverse flow detection state as pending in response to the confidence counter being under the minimum count, wherein the confidence counter is not reset and the method is repeated in the pending state.

In some configurations, the reverse flow indicator can be calculated in response to the confidence counter reaching the minimum count.

In some configurations, determining that the inputs are at steady state for the predetermined period of time can comprise determining one or more of the following inputs are at steady state for the predetermined period of time: a temperature of the humidifier inlet, a temperature of the humidifier outlet, a temperature of a heater plate of the humidifier, and/or a temperature at a patient end of the inspiratory conduit.

In some configurations, the reverse flow indicator can be calculated based at least in part on at least some of the inputs and/or system parameters of the respiratory humidification system.

In some configurations, the reverse flow indicator can be calculated using an equation including one or more of: a temperature at a patient end of the inspiratory conduit, a temperature of the humidifier inlet, a temperature of a heater plate of the humidifier, and/or a power of a heat source of the inspiratory conduit.

In some configurations, the indication of the reverse flow condition can be outputted in response to the reverse flow indicator being greater than 0.

In some configurations, the method can further comprise detecting a sudden flow change in response to the reverse flow indicator exceeding the threshold.

In some configurations, the method can further comprise removing the indication of the reverse flow indication in response to detecting the sudden flow change.

In some configurations, the method can further comprise proceeding to therapy operation after outputting the indication of reverse flow condition.

In some configurations, the method can be performed during therapy operation of the system without interrupting the therapy operation.

In some configurations, the method can be performed continuously.

In some configurations, the present disclosure provides a reverse flow detector of a respiratory humidification system that includes a gases source, a humidifier including an inlet and an outlet, an inspiratory conduit, and a plurality of sensors. The detector can comprise a controller in electrical communication with the plurality of sensors, wherein the controller is configured to: receive inputs from one or more of the plurality of sensors; determine that the inputs are at steady state; calculate a reverse flow indicator based at least in part on at least some of the inputs; and output an indication of reverse flow conditions in response to the reverse flow indicator exceeds a threshold.

In some configurations, the controller can be configured to determine the inputs are determined to be at steady state for a predetermined period of time.

In some configurations, the steady state of the inputs can comprise a rate of change of the inputs under a fluctuation limit for the predetermined period of time.

In some configurations, the controller can be further configured to execute a reset function in response to predetermined system conditions.

In some configurations, the controller can be further configured to determine a humidifier outlet state based on whether a temperature at the humidifier outlet has reached a pre-set limit.

In some configurations, the controller can be configured to calculate the indication of the reverse flow condition using different equations depending on the determined humidifier outlet state.

In some configurations, the different equations can comprise at least one coefficient that is different in the equations.

In some configurations, the controller can be further configured to ignore at least readings from a sensor configured to measure the temperature of the humidifier outlet in response to the determined humidifier outlet state.

In some configurations, the controller can be further configured to update a confidence counter, wherein the counter is incremented in response to the inputs being at steady state for the predetermined period of time.

In some configurations, the controller can be further configured to calculate the reverse flow indicator in response to the confidence counter reaching a minimum count.

In some configurations, the controller can be further configured to update the confidence counter after calculating the reverse flow indicator.

In some configurations, the controller can be further configured to set a reverse flow detection state as pending in response to the confidence counter being under the minimum count, wherein the confidence counter is not reset and the method is repeated in the pending state.

In some configurations, the controller can be further configured to reset the confidence counter to 0 in response to a reset function being executed.

In some configurations, the controller can be further configured to determine that one or more of the following inputs are at steady state for the predetermined period of time: a temperature of the humidifier inlet, a temperature of the humidifier outlet, a temperature of a heater plate of the humidifier, and/or a temperature at a patient end of the inspiratory conduit.

In some configurations, the controller can be configured to calculate the reverse flow indicator based at least in part on at least some of the inputs and/or system parameters of the respiratory humidification system.

In some configurations, the controller can be configured to calculate the reverse flow indicator using an equation including one or more of: a temperature at a patient end of the inspiratory conduit, a temperature of the humidifier inlet, a temperature of a heater plate of the humidifier, and/or a power of a heat source of the inspiratory conduit.

In some configurations, the indication of the reverse flow condition can be outputted in response to the reverse flow indicator being greater than 0.

In some configurations, the controller can be further configured to detect a sudden flow change in response to the reverse flow indicator exceeding the threshold.

In some configurations, the controller can be further configured to remove the indication of the reverse flow indication in response to detecting the sudden flow change.

In some configurations, the controller can be further configured to proceed to therapy operation after outputting the indication of the reverse flow condition.

In some configurations, the controller can be configured to perform the reverse flow detection during therapy operation of the system without interrupting the therapy operation.

In some configurations, the controller can be configured to perform the reverse flow detection continuously.

In some configurations, a humidifier for a humidification system can comprise any configurations of the reverse flow detector described above.

In some configurations, a humidification system can comprise a gases source, a humidifier, and a breathing circuit, wherein the gases source can comprise any configurations of the reverse flow detector described above.

In some configurations, a method of detecting incorrect connections of components in a humidification system can include the steps of detecting reverse flow according to methods disclosed herein and providing an alarm or indication that an incorrect connection exists in the humidification system.

In some aspects a method of detecting a reverse flow condition in a respiratory humidification system including a gases source, a controller, a humidifier, and a breathing circuit. The method can comprise, using the controller of the humidification system, measuring an outlet temperature using a sensor at or near an outlet of a chamber of the humidifier; and in response to detecting at least two trigger events, outputting an indication of a reverse flow condition. The trigger event can comprise the chamber outlet temperature reaching a first threshold temperature. Outputting the indication of the reverse flow condition can be further in response to detecting a pattern of the at least two trigger events.

In some configurations, the method can further comprise starting or restarting a timer in response to detecting a first one of the at least two trigger events.

In some configurations, restarting the timer can be from a time when a trigger event was most recently detected.

In some configurations, the timer can expire after between 5 minute and 120 minutes. The timer can expire after between 5 minutes and 60 minutes.

In some configurations, the timer can expire after between 5 minutes and 30 minutes. The timer can expire after between 5 minutes and 20 minutes.

In some configurations, the timer can expire after between 5 minutes and 10 minutes. The method can further comprise determining whether the timer has expired in response to no trigger event being detected.

In some configurations, the method can further comprise incrementing a counter in response to starting or restarting the timer.

In some configurations, the incrementing the counter can comprise incrementing the counter by a value of 1.

In some configurations, the method can comprise the counter having a value that can be greater than or equal to a counter threshold.

In some configurations, the counter threshold can be between 2 to 20 times. The counter threshold can be between 5 to 15 times.

In some configurations, the counter threshold can be between 5 to 10 times.

In some configurations, the method can further comprise clearing or resetting the outputted indication of the reverse flow condition in response to the counter having a value that can be below the counter threshold.

In some configurations, the method can further comprise resetting the counter in response to a determination that the timer has expired.

In some configurations, the method can further comprise initiating a second method of detecting an indication of a reverse flow condition in response to outputting the indication of the reverse flow condition.

In some configurations, the method can further comprise disabling power to a heater plate of the humidifier and/or a heat source in an inspiratory conduit of the breathing circuit in response to outputting the indication of the reverse flow condition.

In some configurations, disabling power to the heater plate of the humidifier and/or the heat source in the inspiratory conduit can comprise using a safety feature.

In some configurations, the safety feature can comprise a hardware component.

In some configurations, the hardware component can comprise a thermal cut-out.

In some configurations, the hardware component can comprise one or more switches. The switch can comprise a relay. The switch can comprise a transistor.

In some configurations, the safety feature can be electrically coupled with the controller or a different microcontroller.

In some configurations, the outputting the indication of the reverse flow condition further can comprise activating an alarm.

In some configurations, the alarm can be visual and/or audible.

In some configurations, the method can further comprise causing the alarm to be displayed on a user interface of the humidifier and/or the gases source.

In some configurations, the alarm can be activated only after a pre-determined operating time period has been reached.

In some configurations, the first threshold temperature can comprise a chamber outlet cut-out temperature.

In some configurations, the first threshold temperature can be above 37° C.

In some configurations, the first threshold temperature can be between 37.1° C. and 50° C.

In some configurations, the first threshold temperature can be between 38° C. and 45° C.

In some configurations, the first threshold temperature can be between 42° C. and 44° C.

In some configurations, the method further comprising where, in response to detecting a first one of the at least two trigger events, detecting a subsequent one of the at least two trigger events only after the chamber outlet temperature has fallen below a second threshold temperature.

In some configurations, the detecting the first one or the subsequent one of the at least two trigger events can comprise incrementing a counter.

In some configurations, the second threshold temperature can be below the first threshold temperature and above a chamber outlet temperature setpoint.

In some configurations, the detecting the subsequent one of the at least two trigger events only after the chamber outlet temperature has fallen below the second threshold temperature can be configured to provide hysteresis.

In some configurations, the method can be performed during setup of the system or just after setup can be finished.

In some configurations, the method can be performed during steady state operation of the system.

In some configurations, the method can be performed by interrupting steady state operation for a period of time.

In some configurations, the pattern can be based on a predetermined periodicity of the at least two trigger events.

In some configurations, the pattern can comprise using one or more of Fast Fourier Transform, autocorrelation, and/or statistical analysis. The detecting the pattern can comprise using a sliding window.

In some aspects, a reverse flow detector for a humidification system that includes a gases source, a humidifier, and a breathing circuit, and configured to detect a reverse flow condition in the humidification system is disclosed. The detector can comprise a controller configured to receive a sensor signal indicative of an outlet temperature at an outlet of a chamber of the humidifier that carries humidification fluid; and in response to detecting at least two trigger events, output an indication of a reverse flow condition, where a trigger event can comprise the chamber outlet temperature reaching a first threshold temperature. The controller can be configured to output the indication of the reverse flow condition further in response to detecting a pattern of the at least two trigger events.

In some configurations, the controller can be further configured to start or restart a timer in response to detecting a first one of the at least two trigger event.

In some configurations, the controller can be configured to restart the timer from a time when a trigger event was most recently detected.

In some configurations, the timer can expire after between 5 minute and 120 minutes In some configurations, the timer can expire after between 5 minute and 60 minutes.

In some configurations, the timer can expire after between 5 minute and 30 minutes.

In some configurations, the timer can expire after between 5 minute and 20 minutes.

In some configurations, the timer can expire after between 5 minute and 10 minutes.

In some configurations, the controller can be further configured to determine whether the timer has expired in response to no trigger event being detected.

In some configurations, the controller can be further configured to increment a counter in response to starting or restarting the timer.

In some configurations, the controller can be configured to increment the counter by a value of 1.

In some configurations, the pattern can comprise the counter having a value that can be greater than or equal to a counter threshold In some configurations, the counter threshold can be between 2 to 20 times.

In some configurations, the counter threshold can be between 5 to 15 times In some configurations, the counter threshold can be between 5 to 10 times.

In some configurations, the controller can be further configured to clear or reset the outputted indication of the reverse flow condition in response to the counter having a value that can be below the counter threshold.

In some configurations, the controller can be further configured to reset the counter in response to a determination that the timer has expired.

In some configurations, the controller can be further configured to initiate a second method of detecting an indication of a reverse flow condition in response to outputting the indication of the reverse flow condition.

In some configurations, the controller can be configured to output the indication of the reverse flow condition by activating an alarm.

In some configurations, the alarm can be visual and/or audible.

In some configurations, the controller can be further configured to cause the alarm to be displayed on a user interface of the humidifier and/or the gases source.

In some configurations, the alarm can be activated only after a pre-determined operating time period has been reached.

In some configurations, the first threshold temperature can comprise a chamber outlet cut-out temperature.

In some configurations, the first threshold temperature can be above 37° C.

The first threshold temperature can be between 37.1° C. and 50° C.

In some configurations, the first threshold temperature can be between 38° C. and 45° C.

In some configurations, the first threshold temperature can be between 42° C. and 44° C.

In response to detecting a first one of the at least two trigger events, the controller can be further configured to detect a subsequent one of the at least two trigger events only after the chamber outlet temperature has fallen below a second threshold temperature.

In some configurations, the controller can be configured to detect the first one or the subsequent one of the at least two trigger events by incrementing a counter.

In some configurations, the second threshold temperature can be below the first threshold temperature and above a chamber outlet temperature setpoint.

In some configurations, the controller can be configured to detect the subsequent one of the at least two trigger events only after the chamber outlet temperature has fallen below the second threshold temperature to prevent hysteresis.

In some configurations, the detecting can be performed during setup of the system or just after setup can be finished.

In some configurations, the detecting can be performed during steady state operation of the system.

In some configurations, the detecting can be performed by interrupting steady state operation for a period of time.

In some configurations, the controller can be configured to detect the pattern based on a predetermined periodicity of the at least two trigger events.

In some configurations, the controller can be configured to detect the pattern can comprise using one or more of Fast Fourier Transform, autocorrelation, and/or statistical analysis.

In some configurations, the controller can be configured to detect the pattern using a sliding window.

In some configurations, A humidifier for a humidification system, wherein the humidifier can comprise the reverse flow detector.

In some configurations, the controller can be further configured to disable power to a heater plate of the humidifier and/or a heat source in an inspiratory conduit of the breathing circuit in response to outputting the indication of the reverse flow condition.

In some configurations, the humidifier further comprising a safety feature configured to disable power to the heater plate of the humidifier and/or the heat source in the inspiratory conduit in response to outputting the indication of the reverse flow condition.

In some configurations, the safety feature can comprise a hardware component.

In some configurations, the hardware component can comprise a thermal cut-out.

In some configurations, the hardware component can comprise one or more switches.

In some configurations, the switch can comprise a relay.

In some configurations, the switch can comprise a transistor.

In some configurations, the safety feature can be electrically coupled with the controller or a different microcontroller.

In some configurations, a humidification system comprising a gases source, a humidifier, and a breathing circuit, wherein the gases source can comprise the reverse flow detector.

In some configurations, the reverse flow detector can further comprise a sensor providing the sensor signal.

In some configurations, the reverse flow detector and the sensor signal form part of the humidifier.

In some configurations, the reverse flow detector can comprise a memory.

In some configurations, the reverse flow detector can further comprise a sensor located in the breathing circuit, wherein the sensor provides the sensor signal.

In some aspects, a method of detecting reverse flow in a respiratory humidification system including a gases source, a controller, a humidifier including an inlet and an outlet, and an inspiratory conduit is disclosed. The method can comprise, using the controller of the humidification system, determining a first patient end temperature at or near a patient end of the inspiratory conduit and/or a first outlet temperature at or near the outlet of the humidifier; providing an electrical power to an inspiratory conduit heat source in the inspiratory conduit; determining a second patient end temperature at or near the patient end of the inspiratory conduit and a second outlet temperature at or near the outlet of the humidifier after providing the electrical power to the inspiratory conduit heat source; comparing the first patient end temperature with the second patient end temperature and/or comparing the first outlet temperature with the second outlet temperature; in response to the second patient end temperature being greater than the first patient end temperature and/or the second outlet temperature being greater than the first outlet temperature, comparing at least one of: the second patient end temperature with the second outlet temperature, a change in the second patient end temperature with a change in the second outlet temperature over a predetermined time period, the second patient end temperature with a patient end temperature threshold, the second outlet temperature with an outlet temperature threshold, a rate of change in the second patient end temperature with a second patient end temperature rate of change threshold; a rate of change in the second outlet temperature with a second outlet temperature rate of change threshold and/or a rate of change in the second patient end temperature with a rate of change in the second outlet temperature over the predetermined time period; and outputting an indication of reverse flow conditions in response to at least one of: the second patient end temperature being higher than the second outlet temperature, the change in the second patient end temperature being lower than the change in the second outlet temperature over the predetermined time period, the second patient end temperature being lower than the patient end temperature threshold, the second outlet temperature being lower than the outlet temperature threshold, the rate of change in the second patient end temperature being lower than the second patient end temperature rate of change threshold; the rate of change in the second outlet temperature being higher than the second outlet temperature rate of change threshold; and/or the rate of change in the second patient end temperature being lower than the rate of change in the second outlet temperature over the predetermined time period.

In some configurations, the method can further comprise executing a first timeout reset function in response to the method having not been started at an end of a first timeout period.

In some configurations, the method can further comprise proceeding to therapy operation upon executing the first timeout reset function.

In some configurations, the method can further comprise detecting a minimum flow rate of a gases flow in the system prior to determining the first patient end temperature and the first outlet temperature.

In some configurations, the minimum flow rate can be a filtered flow rate.

In some configurations, the minimum flow rate can be about 3 L/min.

In some configurations, the method can further comprise executing a first timeout reset function in response to the gases flow having a flow rate below the minimum flow rate.

In some configurations, the electrical power to the inspiratory conduit heat source can be a maximum electrical power.

In some configurations, the method can further comprise disabling electrical power to a heater plate of the humidifier.

In some configurations, the method can further comprise reducing electrical power to a heater plate of the humidifier to at or below 20% of a duty cycle.

In some configurations, the method can further comprise providing the electrical power to the inspiratory conduit heat source until the second patient end temperature can be greater than the first patient end temperature and/or the second outlet temperature can be greater than the first outlet temperature.

In some configurations, the method can further comprise executing a second timeout reset function in response to the controller providing the electrical power to the inspiratory conduit heat source at an end of a second timeout period.

In some configurations, the method can further comprise proceeding to therapy operation upon executing the second timeout reset function.

In some configurations, the method can further comprise comparing can be in response to the second patient end temperature being greater than the first patient end temperature by a first offset value and/or the second outlet temperature being greater than the first outlet temperature by a second offset value.

In some configurations, the first and/or second offset values are up to about 5° C.

In some configurations, the first and/or second offset values are between about 1.5° C. and about 5° C.

In some configurations, the first and/or second offset values are about 2° C.

In some configurations, the method can be performed during setup of the system.

In some configurations, the setup further can comprise a water-out detection test in response to no reverse flow condition being detected.

In some configurations, the method can be performed during therapy operation of the system.

In some configurations, the method can further comprise resume therapy operation after outputting the indication of reverse flow condition.

In some configurations, the indication can comprise a reverse flow alarm.

In some configurations, the patient end temperature threshold and/or the outlet threshold are at least one or more of a pre-determined value, a predetermined value after a pre-determined period of time, a value corresponding to a rate of change, or a time to reach a predetermined value or rate.

In some configurations, the method can further comprise a sensor which measures the first patient end temperature and/or the inspiratory conduit has a sensor to measure the first outlet temperature.

In some aspects, method of detecting reverse flow in a respiratory humidification system including a gases source, a controller, a humidifier including an inlet and an outlet, and an inspiratory conduit is disclosed. The method can comprise, using the controller of the humidification system, providing an electrical power to an inspiratory conduit heat source in the inspiratory conduit for a predetermined period of time; determining a patient end temperature at or near a patient end of the inspiratory conduit and/or a chamber outlet temperature at or near the outlet of the humidifier after providing the electrical power to the inspiratory conduit heat source for the predetermined period of time; and outputting an indication of reverse flow conditions in response to at least one of: the patient end temperature being lower than the outlet temperature, the patient end temperature being lower than a patient end temperature threshold, the chamber outlet temperature being higher than a chamber outlet temperature threshold, the change in the patient end temperature being lower than the change in the outlet temperature over the predetermined time period, a rate of change in the patient end temperature being lower than a patent end temperature rate of change threshold; a rate of change in a chamber outlet temperature being higher than the chamber outlet temperature rate of change threshold; and/or the rate of change in the patient end temperature being lower than the rate of change in the outlet temperature over the predetermined time period.

In some configurations, the patient end temperature threshold and/or the chamber outlet temperature threshold correspond to one or more of: a pre-determined value; a predetermined value after a predetermined time period; or a time to reach a predetermined value.

In some configurations, the method can further comprise executing a timeout reset function in response to the method having not been started at an end of a timeout period.

In some configurations, the method can further comprise proceeding to therapy operation upon executing the timeout reset function.

In some configurations, the method can further comprise detecting a minimum flow rate of a gases flow in the system prior to determining the first patient end temperature and the first outlet temperature.

In some configurations, the minimum flow rate can be a filtered flow rate.

In some configurations, the minimum flow rate can be about 3 L/min.

In some configurations, the method can further comprise a timeout reset function in response to the gases flow having a flow rate below the minimum flow rate.

In some configurations, the electrical power to the inspiratory conduit heat source can be a maximum electrical power.

In some configurations, the method can further comprise disabling electrical power to a heater plate of the humidifier.

In some configurations, the method can further comprise reducing electrical power to a heater plate of the humidifier.

In some configurations, the method can further comprise reducing electrical power to a heater plate of the humidifier to at or below 20% of a duty cycle.

In some configurations, the method can further comprise comparing the patient end temperature with a baseline patient end temperature, and/or comparing the outlet temperature with a baseline outlet temperature, after providing an electrical power to the inspiratory conduit heat source in the inspiratory conduit for the predetermined period of time, wherein the baseline outlet temperature and/or the baseline patient end temperature were measured before providing an electrical power to the inspiratory conduit heat source.

In some configurations, the electrical power can be provided to the inspiratory conduit heat source until the second patient end temperature can be greater than the first patient end temperature and/or the second outlet temperature can be greater than the first outlet temperature.

In some configurations, the comparing can comprise comparing the patient end temperature with the baseline patient end temperature plus a first offset value and/or the outlet temperature with the baseline outlet temperature plus a second offset value.

In some configurations, the first and/or second offset values are up to about 5° C.

In some configurations, the first and/or second offset values are between about 1.5° C. and about 5° C.

In some configurations, the first and/or second offset values are about 2° C.

In some configurations, the method can be performed during setup of the system.

In some configurations, the setup further can comprise a water-out detection test in response to no reverse flow condition being detected.

In some configurations, the method can be performed during therapy operation of the system.

In some configurations, the method can further comprise resume therapy operation after outputting the indication of reverse flow condition.

In some configurations, the indication can comprise a reverse flow alarm.

In some aspects, a reverse flow detector of a respiratory humidification system is disclosed. The detector can comprise: a controller configured to be in electrical communication with a first sensor and a second sensor, wherein the first sensor can be at or near a patient end of an inspiratory conduit and configured to measure a patient end temperature, and the second sensor can be at or near an outlet of a humidifier and configured to measure an outlet temperature, the inspiratory conduit configured to provide humidified gases to a user and including an inspiratory conduit heat source, the humidifier configured to humidify gases and further including a humidifier heat source to heat a liquid to humidify the gases provided by a gases source; the controller configured to detect an indication of reverse flow conditions in the humidification system by being configured to: determine a first patient end temperature at a patient end of the inspiratory conduit and/or a first outlet temperature at the outlet of the humidifier; provide an electrical power to the inspiratory conduit heat source; determine a second patient end temperature and a second outlet temperature after providing the electrical power to the inspiratory conduit heat source; compare the first patient end temperature with the second patient end temperature and/or compare the first outlet temperature with the second outlet temperature; in response to the second patient end temperature being greater than the first patient end temperature and/or the second outlet temperature being greater than the first outlet temperature, compare at least one of: the second patient end temperature with the second outlet temperature, a change in the second patient end temperature with a change in the second outlet temperature over an associated predetermined time period, the second patient end temperature with a patient end temperature threshold, the second outlet temperature with an outlet temperature threshold; a rate of change in the second patient end temperature with a patient end temperature rate of change threshold; a rate of change in the second outlet temperature with a outlet temperature rate of change threshold;

and/or a rate of change in the second patient end temperature with a rate of change in the second outlet temperature over an associated predetermined time period; and output an indication of reverse flow conditions in response to at least one of: the second patient end temperature being lower than the second outlet temperature, the change in the second patient end temperature being lower than the change in the second outlet temperature over the associated predetermined time period, the second patient end temperature being lower than the patient end temperature threshold, the second outlet temperature being higher than the outlet temperature threshold, the rate of change in the second patient end temperature is higher than a patient end temperature rate of change threshold; the rate of change in the second outlet temperature is higher than the outlet temperature rate of change threshold; and/or the rate of change in the second patient end temperature being lower than the rate of change in the second outlet temperature over the associated predetermined time period.

In some configurations, the controller can be further configured to execute a timeout reset function in response to the method having not been started at an end of a timeout period.

In some configurations, the controller can be further configured to proceed to therapy operation upon executing the timeout reset function.

In some configurations, the controller can be further configured to detect a minimum flow rate of a gases flow in the system prior to determining the first patient end temperature and the first outlet temperature.

In some configurations, the minimum flow rate can be a filtered flow rate.

In some configurations, the minimum flow rate can be about 3 L/min.

In some configurations, the controller can be further configured to execute a timeout reset function in response to the gases flow having a flow rate below the minimum flow rate.

In some configurations, the electrical power to the inspiratory conduit heat source can be a maximum electrical power.

In some configurations, the controller can be further configured to disable electrical power to a heater plate of the humidifier (optionally in response to detection of reverse flow).

In some configurations, the controller can be further configured to reduce electrical power to a heater plate of the humidifier to at or below 20% of a duty cycle (optionally in response to detection of reverse flow).

In some configurations, the controller can be further configured to provide the electrical power to the inspiratory conduit heat source until the second patient end temperature can be greater than the first patient end temperature and/or the second outlet temperature can be greater than the first outlet temperature.

In some configurations, the controller can be further configured to execute a second timeout reset function in response to the controller providing the electrical power to the inspiratory conduit heat source at an end of a second timeout period.

In some configurations, the controller can be further configured to proceed to therapy operation upon executing the second timeout reset function.

In some configurations, the comparing can be in response to the second patient end temperature being greater than the first patient end temperature by a first offset value and/or the second outlet temperature being greater than the first outlet temperature by a second offset value.

In some configurations, the first and/or second offset values are up to about 5° C.

In some configurations, the first and/or second offset values are between about 1.5° C. and about 5° C.

In some configurations, the first and/or second offset values are about 2° C.

In some configurations, the controller can be configured to perform the reverse flow detection during setup of the system.

In some configurations, the setup further can comprise a water-out detection test in response to no reverse flow condition being detected.

In some configurations, the controller can be configured to perform the reverse flow detection during therapy operation of the system.

In some configurations, the controller can be further configured to resume therapy operation after outputting the indication of reverse flow condition.

In some configurations, the indication can comprise a reverse flow alarm. A humidifier for a humidification system, wherein the humidifier can comprise the reverse flow detector. A humidification system comprising a gases source, a humidifier, and a breathing circuit, wherein the gases source can comprise the reverse flow detector.

In some configurations, the patient end temperature threshold and/or the outlet threshold are at least one or more of a pre-determined value, a predetermined value after a pre-determined period of time, or a time to reach a predetermined value.

In some configurations, the reverse flow detector can further comprise the first sensor and the second sensor.

In some aspects, a reverse flow detector of a respiratory humidification system is disclosed. The detector can comprise: a controller configured to be in electrical communication with a first sensor and a second sensor, wherein the first sensor can be at or near a patient end of an inspiratory conduit and configured to measure a patient end temperature, and the second sensor can be at or near an outlet of a humidifier and configured to measure an outlet temperature, the inspiratory conduit configured to provide humidified gases to a user and including an inspiratory conduit heat source, the humidifier configured to humidify gases and further including a humidifier heat source to heat a liquid to humidify the gases provided by a gases source; the controller configured to detect an indication of reverse flow conditions in the humidification system by being configured to: provide an electrical power to an inspiratory conduit heat source in the inspiratory conduit for a predetermined period of time; determine a patient end temperature at or near a patient end of the inspiratory conduit and a chamber outlet temperature at or near the outlet of the humidifier after providing the electrical power to the inspiratory conduit heat source for the predetermined period of time; and output an indication of reverse flow conditions in response to at least one of: the patient end temperature being lower than the outlet temperature, the patient end temperature being lower than a patient end temperature threshold, the chamber outlet temperature being higher than a chamber outlet temperature threshold, a change in the patient end temperature being lower than the change in the outlet temperature over the predetermined time period, the rate of change in the second patient end temperature being lower than the patient end temperature rate of change threshold; the rate of change in the second outlet temperature being higher than the outlet temperature rate of change threshold; and/or the rate of change in the patient end temperature being lower than the rate of change in the outlet temperature over the predetermined time period.

In some aspects, a reverse flow detector of a respiratory humidification system is disclosed. The detector can comprise: a controller configured to be in electrical communication with a first sensor and a second sensor, wherein the first sensor is at or near a patient end of an inspiratory conduit and configured to measure a patient end temperature, and the second sensor is at or near an outlet of a humidifier and configured to measure an outlet temperature, the inspiratory conduit configured to provide humidified gases to a user and including an inspiratory conduit heat source, the humidifier configured to humidify gases and further including a humidifier heat source to heat a liquid to humidify the gases provided by a gases source; the controller configured to detect an indication of reverse flow conditions in the humidification system by being configured to: provide an electrical power to an inspiratory conduit heat source in the inspiratory conduit for a predetermined period of time; determine a patient end temperature at or near a patient end of the inspiratory conduit and a chamber outlet temperature at or near the outlet of the humidifier after providing the electrical power to the inspiratory conduit heat source for the predetermined period of time; and output an indication of reverse flow conditions in response to at least one of: a comparison of the patient end temperature to one or more patient end temperature thresholds, a comparison of the chamber outlet temperature to one or more chamber outlet temperature thresholds, a comparison of the patient end temperature to a chamber outlet temperature.

In some configurations, the comparison of the patient end temperature to a patient end one or more temperature thresholds comprises: the patient end temperature being lower than a patient end temperature threshold, the rate of change of the patient end temperature being lower than a patient end temperature rate of change threshold, the change of the patient end temperature over an associated predetermined time period being lower than a patient end temperature change threshold the maximum rate of change of the patient end temperature being lower than a patient end temperature maximum rate of change threshold, the rise time of the patient end temperature over an associated predetermined time period being higher than a patient end temperature rise time threshold In some configurations, the comparison of the chamber outlet temperature to one or more chamber outlet temperature thresholds comprises: the chamber outlet temperature being higher than a chamber outlet temperature threshold, the rate of change of the chamber outlet temperature being higher than a chamber outlet temperature rate of change threshold, the change of the chamber outlet temperature over an associated predetermined time period being higher than a chamber outlet temperature change threshold the maximum rate of change of the chamber outlet temperature being higher than a chamber outlet temperature maximum rate of change threshold, the rise time of the chamber outlet temperature over an associated predetermined time period being lower than a chamber outlet temperature rise time threshold In some configurations, the comparison of the patient end temperature to a chamber outlet temperature comprises: the chamber outlet temperature being higher than the patient end temperature value, the rate of change of the chamber outlet temperature being higher than the rate of change of the patient end temperature, the change of the chamber outlet temperature over an associated predetermined time period being higher than the change of the patient end temperature over an associated predetermined time period, the maximum rate of change of the chamber outlet temperature being higher than the maximum rate of change of the patient end temperature value, the rise time of the chamber outlet temperature over an associated predetermined time period being lower than the rise time of the patient end temperature over an associated predetermined time period.

In some configurations, at least one of the one or more one or more chamber outlet temperature thresholds and/or one or more patient temperature thresholds are based on one or more of:

flow rate of the gases in the humidifier,
ambient temperature,
therapy type,
conduit type, and/or
expiratory heater wire power.

In some configurations, the patient end temperature threshold and/or the chamber outlet temperature threshold correspond to one or more of: a pre-determined value; a predetermined value after a predetermined time period; or a time to reach a predetermined value.

In some configurations, the controller can be further configured to execute a first timeout reset function in response to the method having not been started at an end of a first timeout period.

In some configurations, the controller can be further configured to proceed to therapy operation upon executing the timeout reset function.

In some configurations, the controller can be further configured to detect a minimum flow rate of a gases flow in the system prior to determining the first patient end temperature and the first outlet temperature.

In some configurations, the minimum flow rate can be a filtered flow rate.

In some configurations, the minimum flow rate can be about 3 L/min.

In some configurations, the controller can be further configured to execute a timeout reset function in response to the gases flow having a flow rate below the minimum flow rate.

In some configurations, the electrical power to the inspiratory conduit heat source can be a maximum electrical power.

In some configurations, the controller can be further configured to disable electrical power to a heater plate of the humidifier (optionally in response to the detection of reverse flow).

In some configurations, the controller can be further configured to reduce electrical power to a heater plate of the humidifier.

In some configurations, the controller can be further configured to reduce electrical power to a heater plate of the humidifier to at or below 20% of a duty cycle.

In some configurations, the controller can be further configured to compare the patient end temperature with a baseline patient end temperature, and/or comparing the outlet temperature with a baseline outlet temperature, after providing an electrical power to the inspiratory conduit heat source in the inspiratory conduit for the predetermined period of time, wherein the baseline outlet temperature and/or the baseline patient end temperature were measured before providing an electrical power to the inspiratory conduit heat source.

In some configurations, the controller can be configured to provide the electrical power to the inspiratory conduit heat source until the second patient end temperature can be greater than the first patient end temperature and/or the second outlet temperature can be greater than the first outlet temperature.

In some configurations, the controller can be configured to compare the patient end temperature with the baseline patient end temperature plus a first offset value and/or the outlet temperature with the baseline outlet temperature plus a second offset value.

In some configurations, the first and/or second offset values are up to about 5° C.

In some configurations, the first and/or second offset values are between about 1.5° C. and about 5° C.

In some configurations, the first and/or second offset values are about 2° C.

In some configurations, the controller can be configured to perform the reverse flow detection during setup of the system.

In some configurations, the setup further can comprise a water-out detection test in response to no reverse flow condition being detected.

In some configurations, the controller can be configured to perform the reverse flow detection during therapy operation of the system.

In some configurations, the controller can be further configured to resume therapy operation after outputting the indication of reverse flow condition.

In some configurations, the indication can comprise a reverse flow alarm.

In some configurations, the reverse flow detector can further comprise the first and second sensors.

In some configurations, a humidifier for a humidification system, wherein the humidifier can comprise the reverse flow detector.

In some configurations, a humidification system comprising a gases source, a humidifier, and a breathing circuit, wherein the gases source can comprise the reverse flow detector.

In some configurations, a humidification system comprising a gases source, a humidifier, and optionally the first and second sensors, the inspiratory conduit, wherein the gases source can comprise the reverse flow detector.

In some aspects, a method of detecting reverse flow in a respiratory humidification system including a gases source, a humidifier including an inlet and an outlet, an inspiratory conduit, and a plurality of sensors is disclosed. The method comprising, using a controller of the system, receiving inputs from one or more of the plurality of sensors; determining that the inputs are at steady state; calculating a reverse flow indicator based at least in part on at least some of the inputs; and outputting an indication of a reverse flow condition in response to the reverse flow indicator exceeding a threshold.

In some configurations, the inputs are determined to be at steady state for a predetermined period of time.

In some configurations, the steady state of the inputs can comprise a rate of change of the inputs under a fluctuation limit for the predetermined period of time.

In some configurations, the method can further comprise executing a reset function in response to predetermined system conditions.

In some configurations, the method can further comprise determining a humidifier outlet state based on whether a temperature at the humidifier outlet has reached a pre-set limit.

In some configurations, the calculating the indication of the reverse flow condition can comprise using different equations depending on the determined humidifier outlet state.

In some configurations, the different equations comprise at least one coefficient that can be different in the equations.

In some configurations, the method can further comprise ignoring at least readings from a sensor configured to measure the temperature of the humidifier outlet in response to the determined humidifier outlet state.

In some configurations, the method can further comprise updating a confidence counter, wherein the counter can be incremented in response to the inputs being at steady state for the predetermined period of time.

In some configurations, the calculating the reverse flow indicator can be performed in response to the confidence counter reaching a minimum count.

In some configurations, the updating the confidence counter can be performed after the calculating the reverse flow indicator.

In some configurations, the method can further comprise setting a reverse flow detection state as pending in response to the confidence counter being under the minimum count, wherein the confidence counter can be not reset and the method can be repeated in the pending state.

In some configurations, the reverse flow indicator can be calculated in response to the confidence counter reaching the minimum count.

In some configurations, the determining that the inputs are at steady state for the predetermined period of time can comprise determining one or more of the following inputs are at steady state for the predetermined period of time: a temperature of the humidifier inlet, a temperature of the humidifier outlet, a temperature of a heater plate of the humidifier, and/or a temperature at a patient end of the inspiratory conduit.

In some configurations, the reverse flow indicator can be calculated based at least in part on at least some of the inputs and/or system parameters of the respiratory humidification system.

In some configurations, the reverse flow indicator can be calculated using an equation including one or more of: a temperature at a patient end of the inspiratory conduit, a temperature of the humidifier inlet, a temperature of a heater plate of the humidifier, and/or a power of a heat source of the inspiratory conduit.

In some configurations, the indication of the reverse flow condition can be outputted in response to the reverse flow indicator being greater than 0.

In some configurations, the method can further comprise detecting a sudden flow change in response to the reverse flow indicator exceeding the threshold.

In some configurations, the method can further comprise removing the indication of the reverse flow indication in response to detecting the sudden flow change.

In some configurations, the method can further comprise proceeding to therapy operation after outputting the indication of reverse flow condition.

In some configurations, the method can be performed during therapy operation of the system without interrupting the therapy operation.

In some configurations, the method can be performed continuously.

In some aspects, a reverse flow detector of a respiratory humidification system that includes a gases source, a humidifier including an inlet and an outlet, an inspiratory conduit, and a plurality of sensors is disclosed.

In some configurations, the detector can comprise a controller in electrical communication with the plurality of sensors, wherein the controller can be configured to: receive inputs from one or more of the plurality of sensors; determine that the inputs are at steady state; calculate a reverse flow indicator based at least in part on at least some of the inputs; and output an indication of reverse flow conditions in response to the reverse flow indicator exceeds a threshold.

In some configurations, the controller can be configured to determine the inputs are determined to be at steady state for a predetermined period of time.

In some configurations, the steady state of the inputs can comprise a rate of change of the inputs under a fluctuation limit for the predetermined period of time.

In some configurations, the controller can be further configured to execute a reset function in response to predetermined system conditions.

In some configurations, the controller can be further configured to determine a humidifier outlet state based on whether a temperature at the humidifier outlet has reached a pre-set limit.

In some configurations, the controller can be configured to calculate the indication of the reverse flow condition using different equations depending on the determined humidifier outlet state.

In some configurations, the different equations comprise at least one coefficient that can be different in the equations.

In some configurations, the controller can be further configured to ignore at least readings from a sensor configured to measure the temperature of the humidifier outlet in response to the determined humidifier outlet state.

In some configurations, the controller can be further configured to update a confidence counter, wherein the counter can be incremented in response to the inputs being at steady state for the predetermined period of time.

In some configurations, the controller can be further configured to calculate the reverse flow indicator in response to the confidence counter reaching a minimum count.

In some configurations, the controller can be further configured to update the confidence counter after calculating the reverse flow indicator.

In some configurations, the controller can be further configured to set a reverse flow detection state as pending in response to the confidence counter being under the minimum count, wherein the confidence counter can be not reset and the method can be repeated in the pending state.

In some configurations, the controller can be further configured to reset the confidence counter to 0 in response to a reset function being executed.

In some configurations, the controller can be further configured to determine that one or more of the following inputs are at steady state for the predetermined period of time: a temperature of the humidifier inlet, a temperature of the humidifier outlet, a temperature of a heater plate of the humidifier, and/or a temperature at a patient end of the inspiratory conduit.

In some configurations, the controller can be configured to calculate the reverse flow indicator based at least in part on at least some of the inputs and/or system parameters of the respiratory humidification system.

In some configurations, the controller can be configured to calculate the reverse flow indicator using an equation including one or more of: a temperature at a patient end of the inspiratory conduit, a temperature of the humidifier inlet, a temperature of a heater plate of the humidifier, and/or a power of a heat source of the inspiratory conduit.

In some configurations, the indication of the reverse flow condition can be outputted in response to the reverse flow indicator being greater than 0.

In some configurations, the controller can be further configured to detect a sudden flow change in response to the reverse flow indicator exceeding the threshold.

In some configurations, the controller can be further configured to remove the indication of the reverse flow indication in response to detecting the sudden flow change.

In some configurations, the controller can be further configured to proceed to therapy operation after outputting the indication of the reverse flow condition.

In some configurations, the controller can be configured to perform the reverse flow detection during therapy operation of the system without interrupting the therapy operation.

In some configurations, the controller can be configured to perform the reverse flow detection continuously.

In some configurations, a humidifier for a humidification system, wherein the humidifier can comprise the reverse flow detector.

In some configurations, a humidification system comprising a gases source, a humidifier, and a breathing circuit, wherein the gases source can comprise the reverse flow detector.

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Throughout this disclosure, the term "circuit" or "breathing circuit" may refer to a gases pathway that is configured to transport gases and generally includes one or more conduits that are interconnected to define a gases path. The circuit may also include a humidification chamber, which also forms part of the gases pathway.

Throughout this disclosure, the term "conduit" may refer to an individual component of a gases pathway or circuit, and may be a tube with connectors on both ends of the tube.

Throughout this disclosure, the terms "inlet," "outlet," "inspiratory conduit," "expiratory conduit," "dryline" or "dryline conduit," "patient end," "upstream," "downstream" and the like refer to the intended gases pathway coupling and normal flow direction, regardless of the actual coupling and flow direction.

Throughout this disclosure, a controller can be one or more hardware processors executing software instructions that cause the one or more hardware processors to perform tasks specified by the software programming.

Example Humidification Systems

Figure 1:
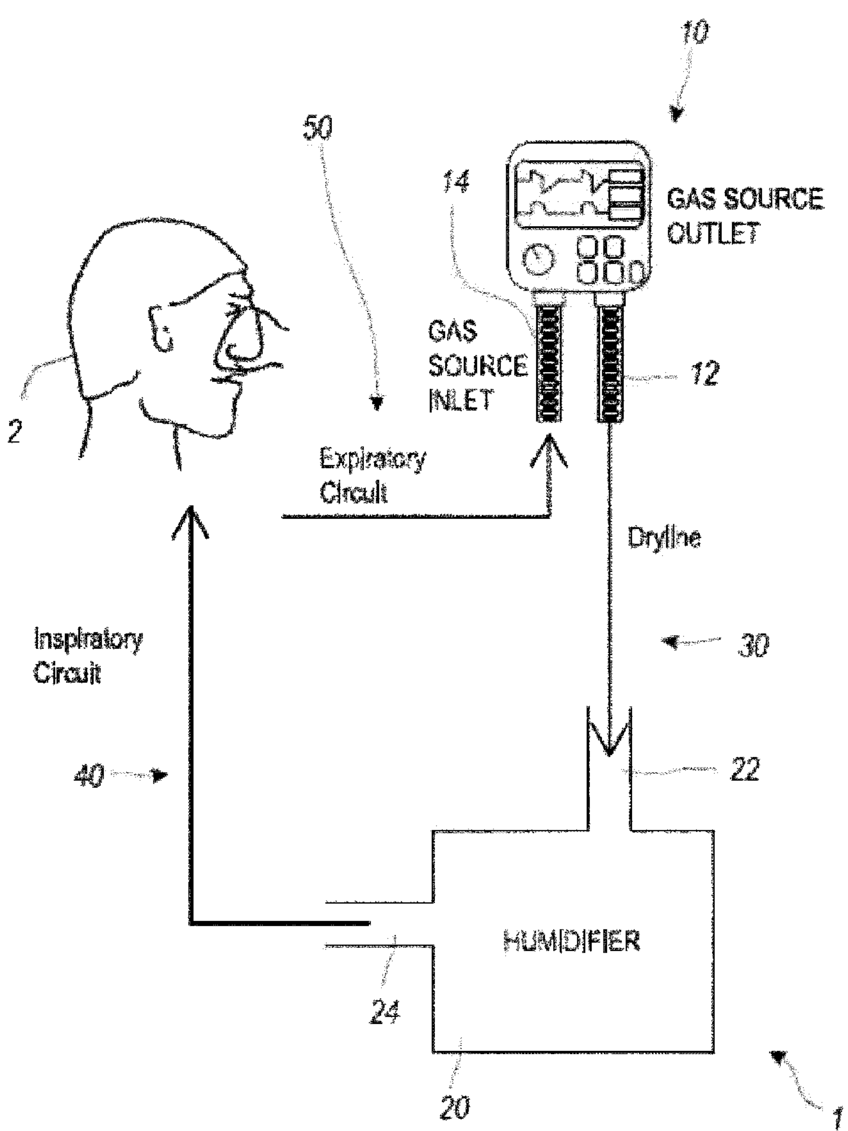
FIGS. 1 and 1A illustrate schematic representations of a dual-limb humidification system.
Figure 1A:
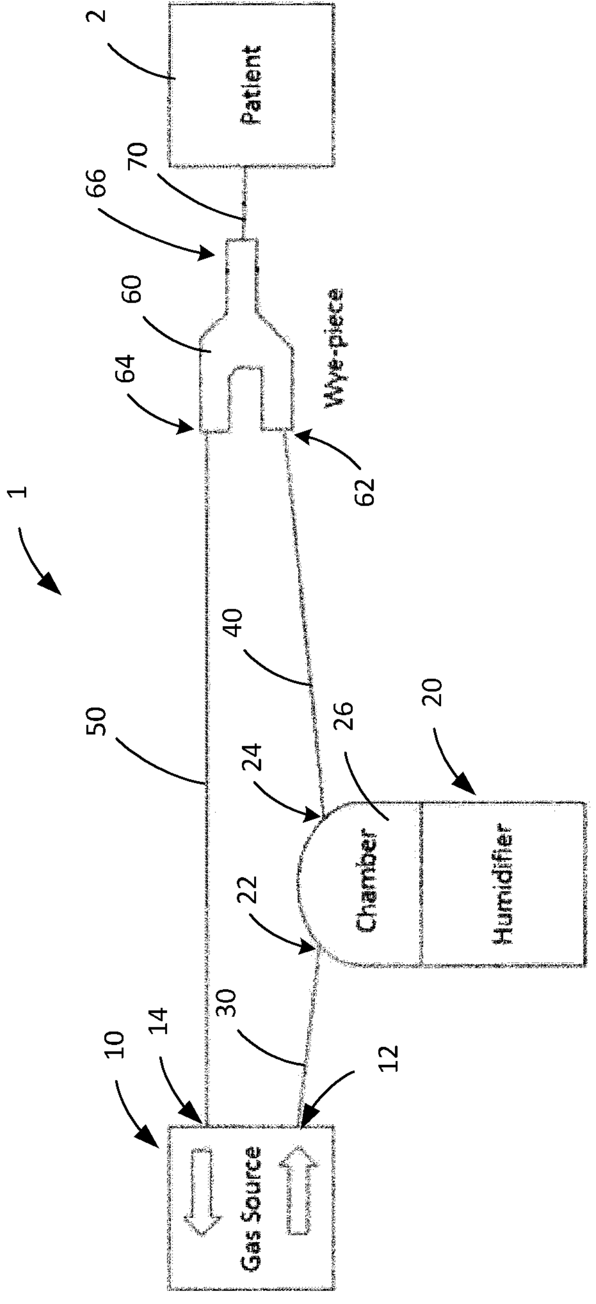

FIGS. 1 and 1A illustrate schematic representations of an example dual-limb humidification system 1. The humidification system 1 can include a gases source 10 in fluid communication with a humidifier 20 via a dryline conduit 30. The gases source can include a flow generator. In this disclosure the example of a gases source is a ventilator, for example, a ventilator configured to entrained ambient air. Other gases sources may also be contemplated, for example, a wall gases source or a compressed gas tank. Supply of gases can be, for example, ambient air and/or from a wall/bottle source (such as oxygen). The gases sources may provide gases to the patient and withdraw gases from the patient, especially when the patient is sedated to simulate breathing and to encourage gases exchange within the patient.

The dual-limb systems thus generally require an inspiratory conduit 40 and an expiratory conduit 50. The gases source can also include a high flow gases source configured to deliver high flow of air or gases, for example, in excess of 30 L/min and/or up to 150 L/min. The gases source can be configured to deliver gases flow rates in other ranges e.g. for neonatal applications the flow rates can be less than 8 L/min. Gases supplied by the gases source can include either dry air, ambient air, oxygen, and/or a mixture of gases (for example, therapeutic gases or breathing gases). One or more controllers, for example, one or more controllers of the gases source 10, can control the gases source 10 to generate a gases flow at a desired flow rate, temperature, and/or pressure. The gases from a gases source outlet 12 can optionally include dry gases.

The dryline conduit 30 can be a tube that is shaped and configured to transfer gases from a gases source to the humidifier 20. The "dryline conduit" refers to a conduit (for example, a tube or a corrugated tube) that is used to transport unhumidified (for example, dry or ambient) gases from the gases source to an inlet 22 of the humidifier 20. When correctly connected (that is, in an operational configuration) the dry line conduit pneumatically connects between the gases source and the humidifier.

The humidifier 20 can include various components, including, for example, a chamber 26 (see FIGS. 1A, 1B and 1C), and a heat source. The heat source can include a humidifier heat source that is used to heat the contents of the chamber 26 in order to vaporize the contents of the chamber 26 such that the gases flowing through the chamber can be humidified by the vaporized contents. In one example the heat source is used to heat and vaporize water to humidify the gases. The heat source also heats the gases passing through the chamber 26 to a desired temperature (for example, a therapeutic temperature). Examples of the humidifier heat source can include chemical heaters, radiant heaters, induction heaters, and the like. By way of example, the heat source can be a heater plate using a resistive heater.

The humidifier 20 can also optionally include one or more processors, such as hardware and/or software processors. The humidifier 20 can include a controller that can include one or more processors and memory. The controller can control operation of the humidifier 20, for example, the steady state operation of the humidifier 20.

The dry gases can be provided to a humidifier inlet 22 via the dryline conduit 30. The humidifier inlet 22 can include a humidifier inlet temperature sensor and/or flow sensor. The chamber 26 of the humidifier 20 can contain a liquid, such as water. Water can be supplied to the humidifier 20 from a water source. The humidified gases can leave a humidifier outlet 24 and enter the inspiratory conduit 40. The humidifier outlet 24 can comprise a humidifier outlet temperature sensor, humidity sensor, and/or flow rate sensor. The humidifier inlet 22 and outlet 24 can be the humidification chamber 26 inlet and outlet, respectively.

The inspiratory conduit 40 (that is, gases delivery conduit) can provide the humidified gases to a patient 2. The inspiratory conduit 40 can be a gas delivery conduit that carries gases from the humidifier to a patient interface 70. The inspiratory conduit 40 (that is, gas delivery conduit) can pneumatically couple the patient interface 70 and the humidifier 20. The inspiratory conduit 40 can be coupled to a patient interface 70. Although the patient 2 is illustrated as wearing a mask in FIG. 1, a person of ordinary skill in the art would appreciate from the disclosure herein that the patient 2 can be wearing other types of patient interfaces 70 disclosed herein, such as a nasal cannula or an endotracheal tube. The patient interface 70 can also include an interface tube, which is a short section of tube, which may be heated or unheated, and the inspiratory conduit 40 can be coupled or connected to the interface tube. The short section of tube may be a breathable tube. The short section of tube can decouple the patient interface from the inspiratory conduit to prevent the patient interface from being dislodged. Alternatively, the inspiratory conduit 40 can be coupled to a wye-piece 60 (see FIG. 1A) at an inspiratory conduit connection port 62. The wye-piece 60 can be connected to the patient interface 70 at a patient interface connection portion 66. Optionally, the inspiratory conduit 40 can include a heater.

A patient interface end of the inspiratory conduit 40 can include a patient end temperature sensor, humidity sensor, and/or flow rate sensor. The inspiratory conduit 40 can have an inspiratory heat source to reduce or prevent condensate formation. Examples of the inspiratory conduit heat source can include a heater wire, heating tape, and/or water jacket heating. Condensate can be formed when a temperature of the humidified gases leaving the humidifier 20 drops below the dew point temperature due to heat loss when the gases travel through an unheated inspiratory conduit 40.

The humidification system 1 can include an expiratory conduit 50 (that is, a gases transport conduit or expired gases transport conduit). The expiratory conduit 50 can be a gas transport conduit that directs gases away from the patient. The expiratory conduit 50 can direct expired gases away from the patient and transport the expired gases to the gases source or to some other device (for example, a vent) that may release the gases to atmosphere. The expiratory conduit 50 can direct gases expired from the patient 2 back to a gases source inlet 14. The expiratory conduit 50 can include an expiratory conduit heat source, such as a heater wire, heating tape, and/or water jacket heating. Optionally, the expiratory conduit 50 can be formed of a breathable material such that moisture within the expired gases are transferred from the expired gas to the atmosphere. In this regard, gases can be dried while travelling through the expiratory conduit 50. The expiratory conduit 50 can be coupled to the patient interface 70 via the wye-piece 60 at the expiratory conduit connection portion 64.

Sensors can be placed in various locations in the humidification system. For example, the sensors can include flow rate, pressure, temperature, and/or humidity sensors. The sensors can comprise a thermistor. The thermistor can act as a temperature sensor and can be switched to act as a flow sensor by applying a voltage to the thermistor to heat the thermistor. Output of the sensors can be received by the controllers to assist the controllers to operate the humidification system 1 in a manner that can provide optimal therapy. Other sensors that may be used include thermocouples, thermostats, semiconductor sensors, infrared sensors, and resistive temperature devices. Types of humidity sensors that may be used can include capacitive humidity sensor, chilled mirror hygrometer, dry bulb humidity sensor, wet bulb humidity sensor, and the like.

Figure 1B:
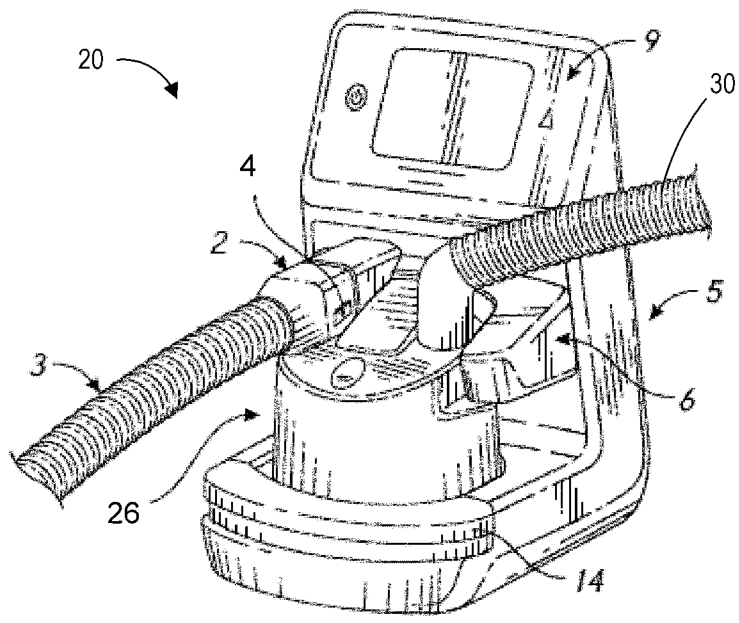
FIGS. 1B and 1C illustrate perspective views of certain components of an example dual-limb humidification system, with some features removed in FIG. 1C to show additional detail.
Figure 1C:
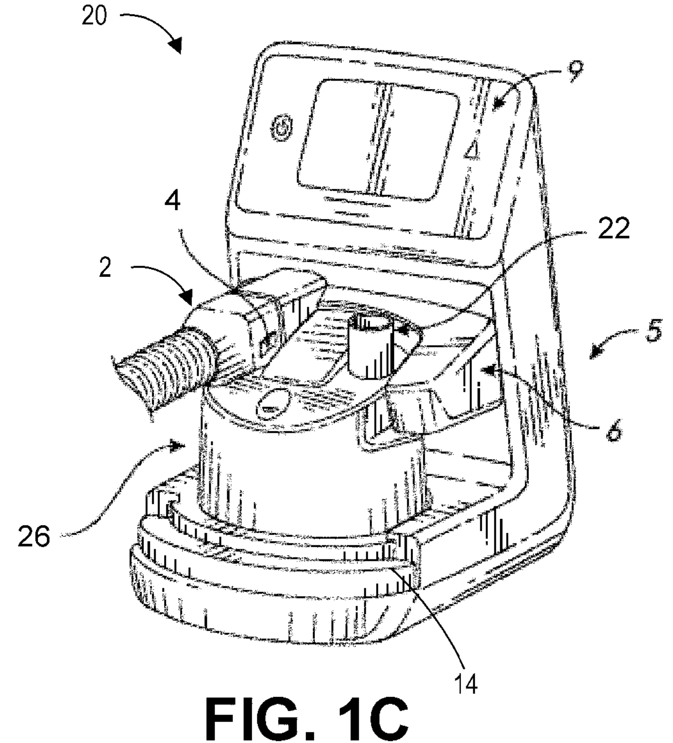

FIG. 1B illustrates an example humidifier 20 connected to an example inspiratory conduit 40 and an example dryline conduit 50. FIG. 1C illustrates the humidifier of FIG. 1B connected to the inspiratory conduit 40, but not to a dryline conduit. Features in FIGS. 1 and 1A can be incorporated in features in FIGS. 1B and 1C, and vice versa.

The humidifier 20 can include a circuit connector 2 that can pneumatically connect the inspiratory conduit 40 to the outlet (not visible in FIGS. 1B and 1C) of the humidification chamber 26. The outlet of the chamber 26 may terminate in a substantially horizontal portion that is angled away from a base unit 5 of the humidifier 20 when the humidification chamber 26 is installed on the base unit 5. The inspiratory conduit 40 may be configured to deliver humidified gases to a user (who can be a patient), such as via a patient interface (not shown). As shown in FIG. 1C, the inlet 22 of the humidification chamber 26 can be configured to be fluidly connected to the gases source (not shown). As shown in FIG. 1B, the inlet 22 of the chamber 26 may be pneumatically coupled to the dryline conduit 30.

The circuit connector 2 can facilitate electrical connection between the inspiratory conduit 40 (for example, the heat source and/or sensors located at the inspiratory conduit 40) to the base unit 5 via a coupler 6. The term "electrical connection" is used to distinguish from "pneumatic connection" and should not be construed in a limiting way. For example, light signals via optical fibers may be communicated. Consequently, the circuit connector 2 may more generally communicatively and/or electrically connect the inspiratory conduit 40 (and any associated peripheral equipment, such as sensors, for example) to the base unit 5, such as via the coupler 6. The coupler 6 may be integrally formed with the base unit 5 or may be a separate, replaceable module or cartridge. The ability to interchange replaceable modules may advantageous in enabling use of different forms of humidification chamber and/or circuit connector. Additionally or alternatively, by including control circuitry, the module may be reconfigured to alter the operation of the humidification apparatus 1.

The circuit connector 2 may include at least a button or switch 4, which may be manually depressed to enable the circuit connector 2 (and hence also the inspiratory conduit 40) to be disconnected from the humidification chamber 26. As will become apparent herein, the circuit connector 2 and the outlet of the humidification chamber 26 may become lockably engaged on connection therebetween with the at least one button or switch 4 being used to subsequently allow for disengaging the circuit connector 2 from the humidification chamber 26. Any suitable connection may be used.

The base unit 5 can include a panel 9, which may be used to mount a user display and/or controls. For example, various dials, switches, and other input means may be used to control operation of the device. Additionally or alternatively, a touch screen display may be used. The user display may display parameters of the system, warnings in the event of any errors or malfunctions, or prompts where user action is required, etc. Where a touch screen display is used, the same display may be used to present information to a user and receive inputs from a user, at least in part.

The base unit 5 can include a heater plate, which is controllably powered to heat the contents of the humidification chamber 26. To achieve more rapid heating, the humidification chamber 26 may include a base plate formed from a highly heat conductive material. Further, to ensure a good connection between the base plate of the humidification chamber 26 and the heater plate, the two surfaces may be biased towards each other. For example, a lip can extend outwards from, or proximate to, the base plate of the humidification chamber 26 and be received under a projecting rim of the base unit 5 as the humidification chamber 26 is slid onto the base unit 5. The heater plate may be spring mounted such that the heater plate is urged upwards into the base plate of the humidification chamber 26, with the lip acting against the projecting rim.

Referring again to FIG. 1B, the base unit 5 can include a sprung latch bar 14. The latch bar 14 can be depressed (see FIG. 1C) to engage and/or disengage the humidification chamber 26 with the base unit 5. When the humidification chamber 26 is fully engaged with the base unit 5, the latch bar 14 can raise and act as a mechanical stop to prevent unintended removal of the humidification chamber 26 from the base unit 5. The outlet of the humidification chamber 4 may be oriented so as to be substantially parallel to the direction of motion of the humidification chamber 26 as it is slid on or off of the base unit 5, at least at the end of the outlet distal from the humidification chamber 26. By configuring the humidifier 20 in this way, it is possible to assemble the circuit connector 2, the humidification chamber 26, and the base unit 5 by either engaging the humidification chamber 26 with the base unit 5 and then attaching the circuit connector 2 to the outlet of the humidification chamber 26, or attaching the circuit connector 2 to the outlet of the humidification chamber 26 and then engaging the humidification chamber 26 with the base unit 5.

Example Incorrect Connection Conditions

Example methods of detecting incorrect flow conditions in a humidification system, such as the humidification system 1 components will now be described with respect to FIGS. 2A-D. These are examples only, and it should be appreciated that other conduit incorrect connections may be possible, such as connecting conduits backwards and/or in different locations in the circuit to where they should normally be connected. The reverse flow detection methods disclosed herein may detect or suggest one or more types of potential incorrect connections.

A control system of the humidification system can generate an alarm or indication that an incorrect connection exists in the humidification system. The alarm or indication may be presented to a user via the user interface. The user interface may include a touchscreen or a combination of screen and buttons. The user interface may be a user interface of the humidifier, a user interface of the gases source, and/or a user interface of a patient monitoring station. The alarm may be communicated from the humidifier to the gases source and/or the patient monitoring station.

The controller of the humidifier may be configured to transmit a control signal to the gases source to switch off the gases source, or reduce the gases source output, or change operation of the gases source to a safe mode if a reverse flow condition is detected. The controller of the humidifier may be configured to reduce power to the heater plate or control the humidifier to reduce humidity output if a reverse flow condition is detected.

Figure 2A:
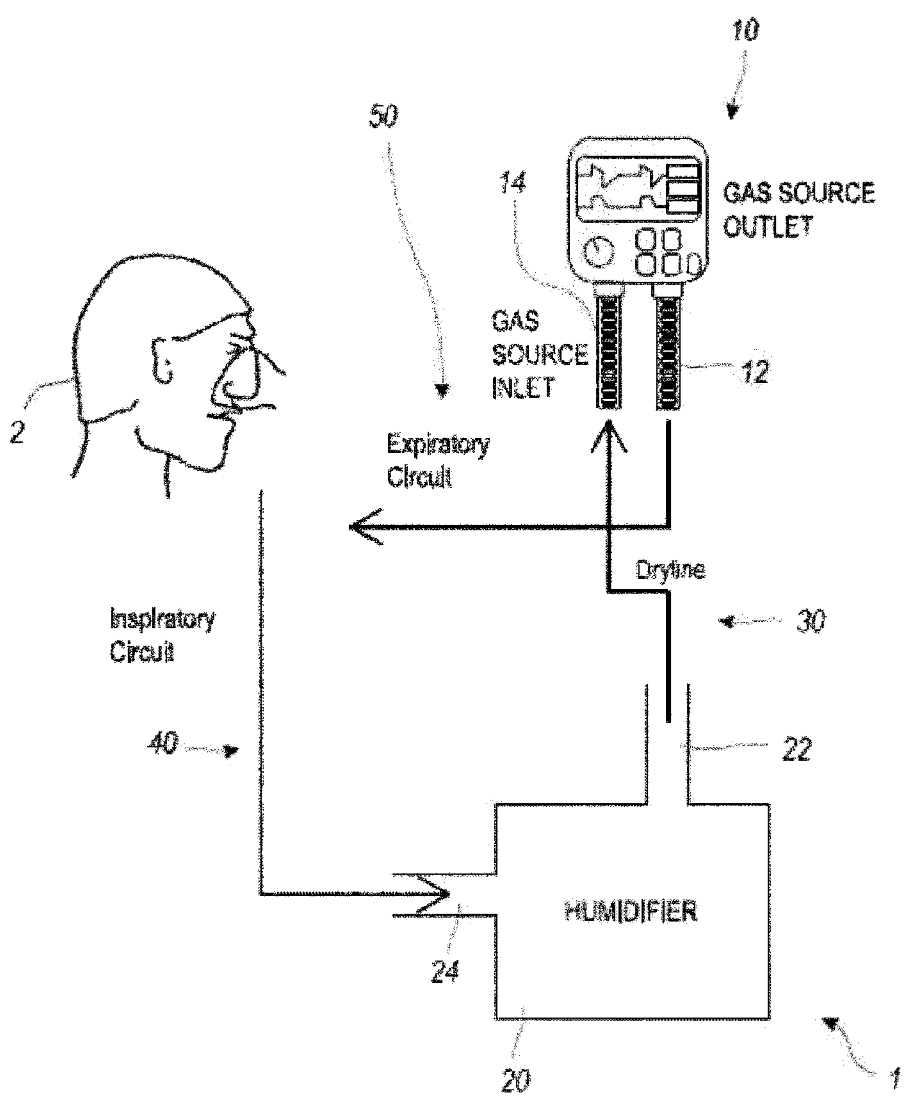
FIGS. 2A-2D illustrate example connection errors and/or incorrect connections in the humidification systems of FIGS. 1 and 1A-1C.

In Error 1 as shown in FIG. 2A, connections of the dryline conduit 30 and the expiratory conduit 50 with the gases source 10 are reversed. Specifically, the dryline conduit 30 is incorrectly coupled to the gases source inlet 14 and the expiratory conduit 50 is incorrectly coupled to the gases source outlet 12. As a result, the dry gases can flow directly to the patient 2 in the expiratory conduit 30 without being humidified or heated because the dry gases do not pass through the humidifier 20. The dry gases can be heated by an expiratory heat source in the expiratory conduit 50, wherein the heating is not properly regulated by the controllers. Expired gases from the patient 2 can become humidified through the humidifier before returning to the gases source 10, resulting in condensation forming in the gases source 10.

Figure 2B:
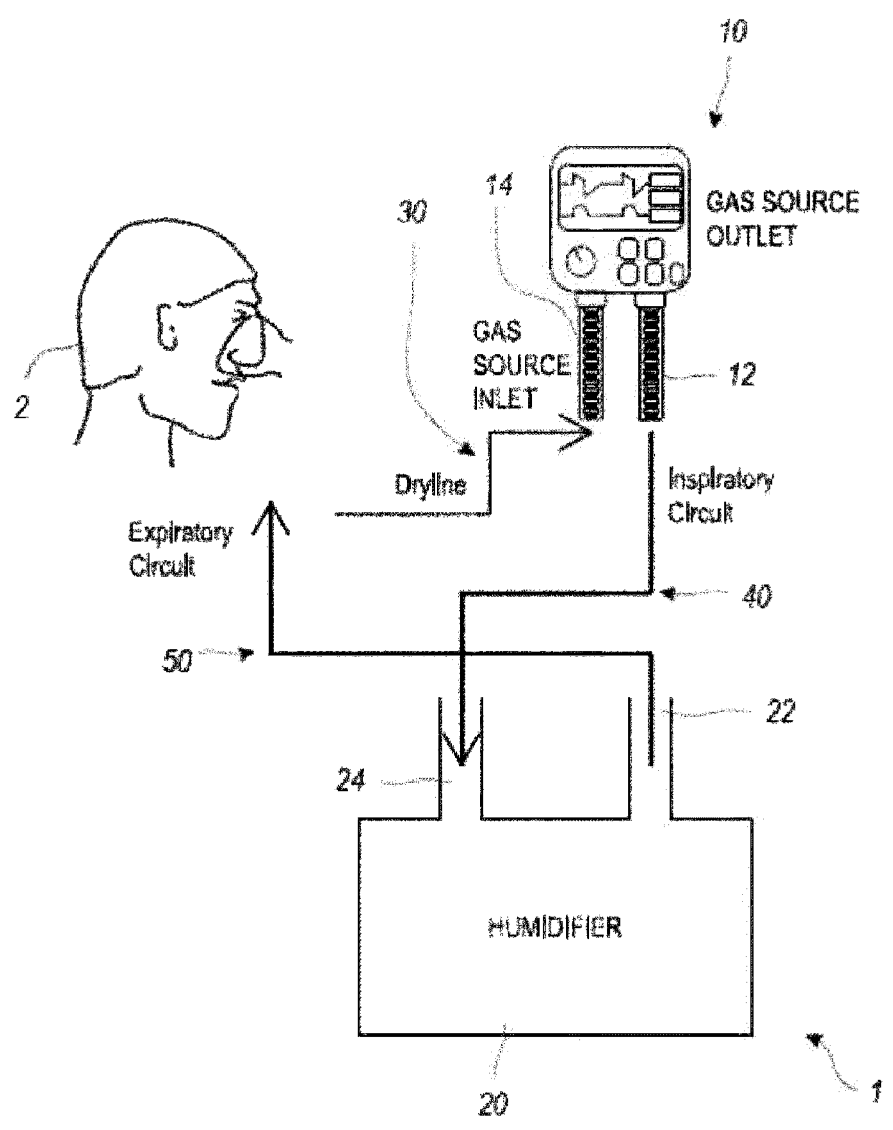

In Error 2 as shown in FIG. 2B, there is an incorrect flow condition in the humidifier 20. Specifically, the inspiratory conduit 40 is incorrectly coupled to the gases source outlet 12 and the humidifier outlet 24, rather than humidifier outlet 24 and patient 2. The expiratory conduit 50 is incorrectly coupled to the humidifier inlet port 22 and the patient 2, rather than patient 2 and gases source 10. The dryline conduit 30 is incorrectly coupled to the patient 2 and the gases source inlet 14, rather than gases source outlet 12 and humidifier inlet 22. The system receives outputs from the patient end sensor in the inspiratory conduit 40 and the sensors at the humidifier inlet and/or outlet 22, 24 that are not indicative of the actual patient end temperature, and/or inlet/outlet temperatures. The humidifier heat source and the inspiratory heat source may not function properly because of the incorrect outputs from the sensors, due to the incorrect feedback from the sensors. The gases leaving the humidifier inlet 22 for the patient 2 may not be heated because the expiratory conduit 50 may not have a heating wire, or may be heated by an expiratory conduit heat source in the expiratory conduit 50, wherein the heating is not properly regulated by the controllers. The expiratory conduit 50 transporting humidified gases from the humidifier 20 can cause the gases to lose moisture (that is, be dried out) before reaching the patient 2.

Figure 2C:
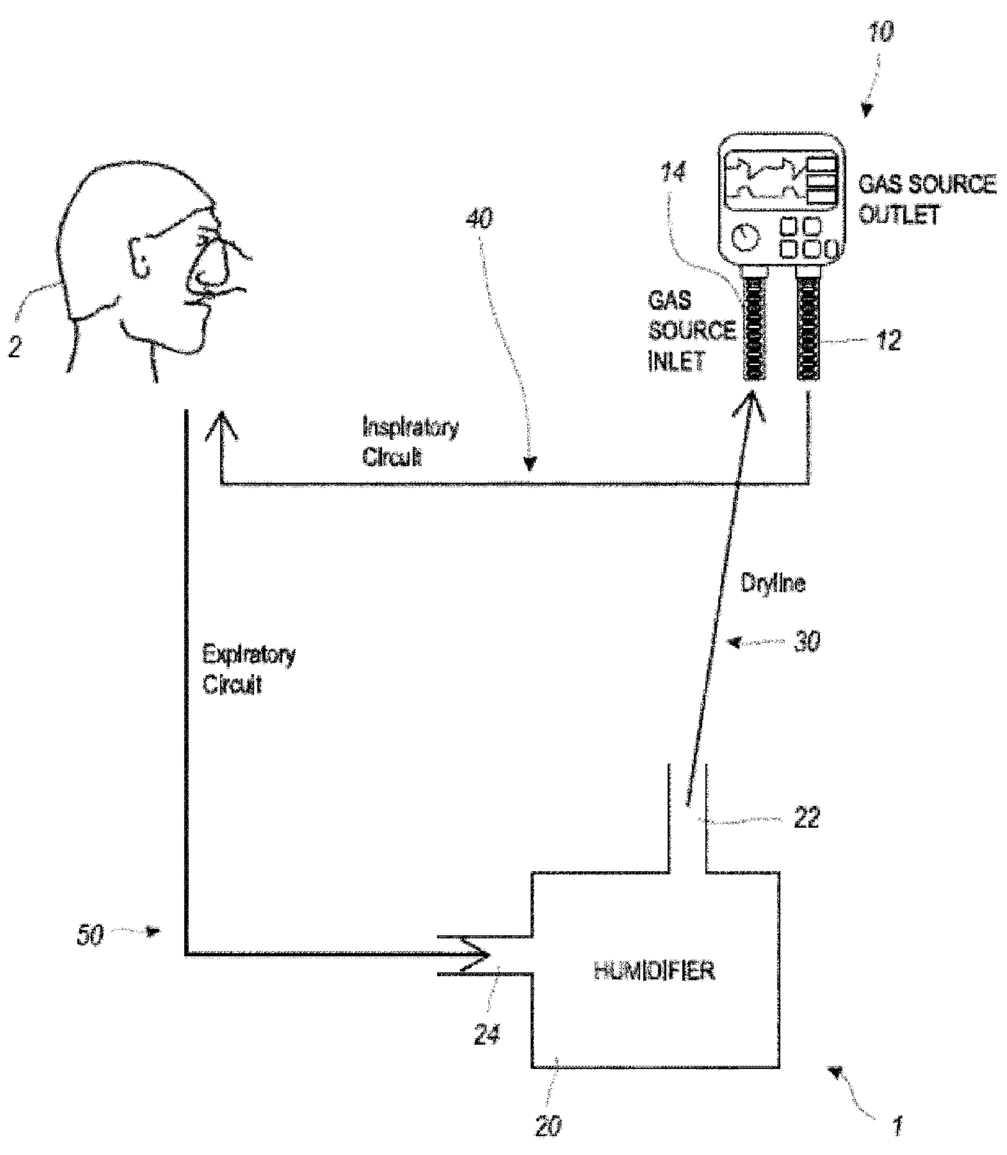

In Error 3 as shown in FIG. 2C, one of the errors includes connections of the gases source inlet 14 and outlet 12 being reversed. Specifically, the dryline conduit 30 is incorrectly coupled to the gases source inlet 14 and the humidifier inlet 22. Another error is that the expiratory conduit 50 is incorrectly coupled to the humidifier outlet 24 and the patient 2. Another error is that the inspiratory conduit 40 is incorrectly coupled to the patient 2 and the gases source inlet 12. As a result, the dry gases can flow directly to the patient 2 in the expiratory conduit 30 without being humidified or heated because the dry gases do not pass through the humidifier 20. The expired gases from the patient 2 can become humidified in the humidifier 30 before returning to the gases source 10. The configuration shown in FIG. 2C can result in humidified gases returning to the gases source without any drying of the gases. The excess moisture in the gases can potentially cause damage to the gases source due to condensation.

Figure 2D:
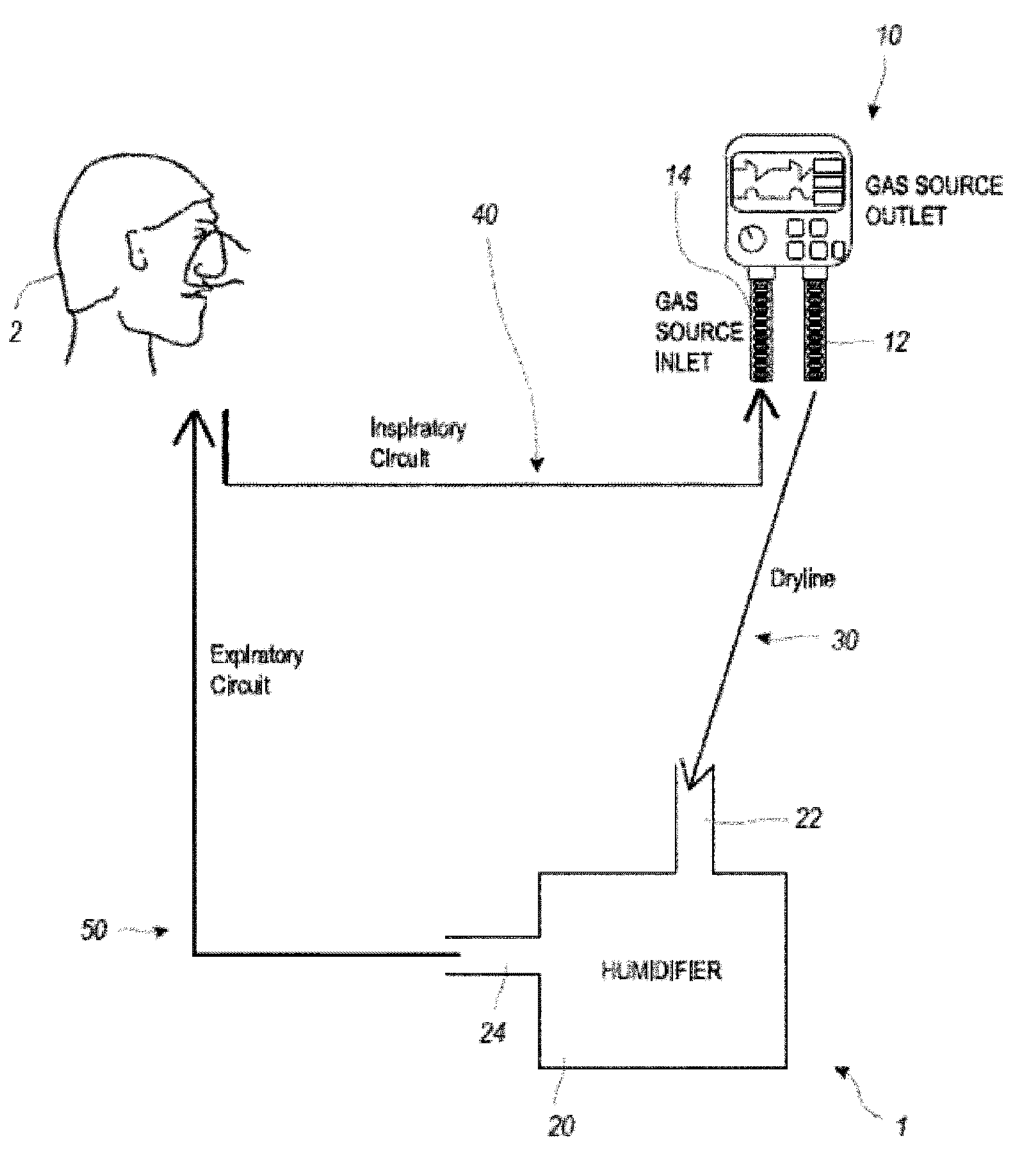

In Error 4 as shown in FIG. 2D, the gases flow in the normal direction, but there are errors in the connections. Specifically, the expiratory conduit 50 is incorrectly coupled to the humidifier outlet 24 and the patient 2. The inspiratory conduit 40 is incorrectly coupled to the gases source inlet 14 and the patient 2. That is, the inspiratory conduit 40 and expiratory conduit 50 have been switched from their intended positions in the breathing circuit. As a result, the patient end sensor in the inspiratory conduit 40 cannot properly measure the temperature of the gases delivered to the patient 2, but measures the temperature of the exhaled gases from the patient 2. The gases leaving the humidifier 20 cannot be heated to ensure that the patient end temperature reaches the patient end set-point. This can be due to the expiratory conduit 50 not having a heat source, or the expiratory conduit heat source not being properly energized by the controllers receiving the patient end temperature input from the sensor in the inspiratory conduit 40. The gases reaching the patient 2 can exceed or fall below the patient end set-point as the gases travel through the expiratory conduit 50. In the case of a breathable expiratory conduit, the gases delivered to the patient will also have sub-optimal humidity. The configuration shown in FIG. 2D can result in humidified gases delivered to the gases source 10. The inspiratory conduit 40 transporting expired gases may not be able to dry the gases like the expiratory conduit 50. Therefore, humidity can be retained in the inspiratory conduit 40 (incorrectly coupled to the gases source inlet 14 and the patient 2) and the moisture can be delivered to the gases source 10. As discussed above, this moisture can potentially cause damage to the gases source 10 due to condensation.

Example Reverse Flow Detection Processes Based on Humidification Chamber Outlet Cut-Out Feature In respiratory therapy, for example, in an invasive or high flow therapy mode, the patient end set point, that is, the temperature set point of the inspiratory conduit at the patient end, can be at about or higher than the normal human body temperature. For example, in the invasive therapy mode, the patient end set point can be about 40° C. and the humidification chamber outlet set point can be about 37° C. In another example, in the high flow therapy mode, the patient end set point can be about 36-40° C. and the humidification chamber outlet set point can be about 33-42° C. As the patient receiving the respiratory therapy can have a body temperature of about 37° C., the air exhaled by the patient can be at or slightly below 37° C. If a reverse flow condition is present, such as shown in FIG. 2A or FIG. 2D, the exhaled air can be received at the patient end of the inspiratory conduit, leading to the patient end temperature falling below the patient end set point. When the exhaled gases flow from the patient to the humidifier in a reverse flow condition, the inspiratory conduit heat source can be activated to heat the gases up to a first inspiratory conduit heat source duty cycle. This is because the controller is programmed to supply power to the inspiratory conduit heat source if the patient end temperature is less than the patient end set point. The controller may be configured to make the patient end temperature reach the set point even in reverse flow conditions, at least because the controller in some humidification systems may not be configured to detect reverse flow conditions.

The respiratory humidification system can include a safety feature to prevent the temperature in the humidification system reaching an undesirably high temperature. The safety feature can switch off power to the heater plate and/or the inspiratory conduit heat source if a trigger event is detected. For example, the trigger event may be the chamber outlet temperature reaching a first threshold temperature. The first threshold temperature can be a chamber outlet cut-out temperature. The safety feature can include a hardware component, such as a thermal cut-off or cut-out, or one or more switches. The switch can include mechanical switches, such as a relay, or electrical switches, such as a transistor, which can include for example, a MOSFET, BJT, or otherwise. The detection of the trigger event may be implemented in the controller of the humidification system and/or another microcontroller. The detection of at least two trigger events may result in a detectable pattern which correlates with an indication of a reverse flow condition. An indication of a reverse flow condition being present can be outputted in response to detecting this pattern.

Figure 3:
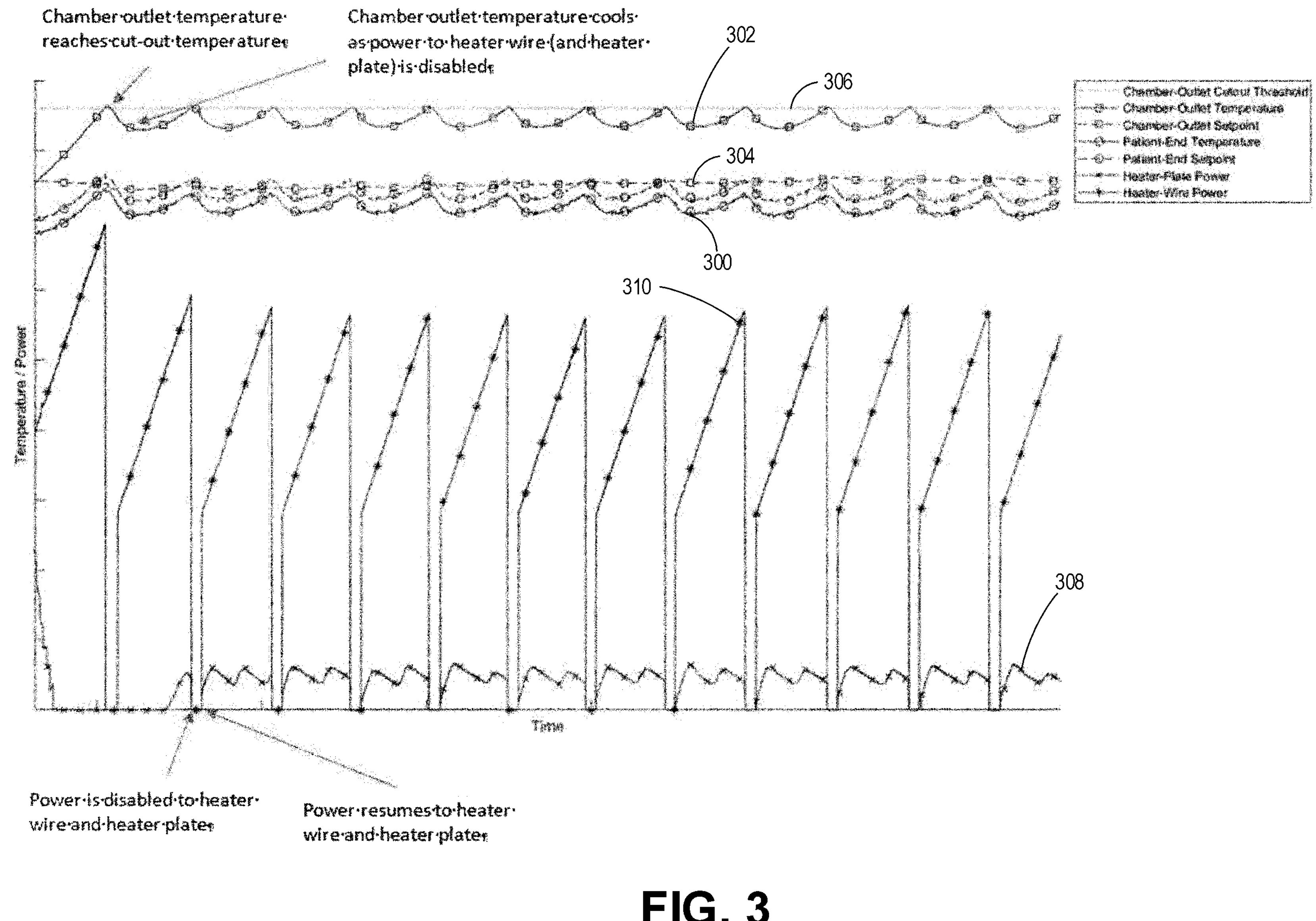
FIG. 3 illustrates an example graph of various temperatures and/or power in a humidification system under a reverse flow condition.

After the inspiratory conduit heat source is activated in a reverse flow condition, the gases at the chamber outlet can reach a temperature that exceeds the first threshold temperature. As shown in FIG. 3, the patient end temperature 300 can be lower than the chamber outlet temperature 302 because the gases are being heated by the inspiratory conduit heat source as the gases travel from the patient to the chamber outlet. As also shown in FIG. 3, the chamber outlet temperature 302 can also be above the chamber outlet temperature set point 304.

As described above, the safety feature can switch off power to the heater plate 308 and/or inspiratory conduit heat source 310 if a trigger event is detected. Also as described above, the trigger event can be the chamber outlet temperature 302 reaching the first threshold temperature 306, which can be higher than the chamber outlet set point 304. In the example shown in FIG. 3, the threshold temperature 306 represents a chamber outlet cut-out temperature. The first threshold temperature 306 can be, for example, above 37° C., or between about 37.1° C. and about 50° C., or between about 38° C. and about 45° C., or between about 42° C. and about 44° C.

A second threshold temperature (not shown), which may be lower than the first threshold temperature 306, may be implemented to provide hysteresis by preventing unnecessary occurrences of trigger events being detected. In a non-limiting example, only one trigger is detected if the chamber outlet temperature 302 remains above the second cut-out temperature. In this example, another trigger event may be detected after the chamber outlet temperature 302 has fallen below the second cut-out temperature.

As shown in FIG. 3, because the gases are travelling from the patient to the chamber outlet during the reverse flow condition, the safety feature which switches off power to the inspiratory conduit heat source 310 can lead to a decrease in the chamber outlet temperature 302. The chamber outlet temperature 302 can cool down to a lower temperature that is below the chamber outlet cut-out temperature 306 before power to the heater plate 308 and/or power to the inspiratory conduit heat source 310 is resumed. As power to the inspiratory conduit heat source 310 (and/or power to the heater plate 308) is resumed, the inspiratory conduit heat source again heats up the gases travelling from patient end to the chamber outlet, causing the chamber outlet temperature 302 to again reach the chamber outlet cut-out temperature 306. As shown in FIG. 3, power to the heater plate 308 and power to the inspiratory conduit heat source 310 can repeatedly be cut off and resumed, resulting in a detectable pattern.

Figure 4:
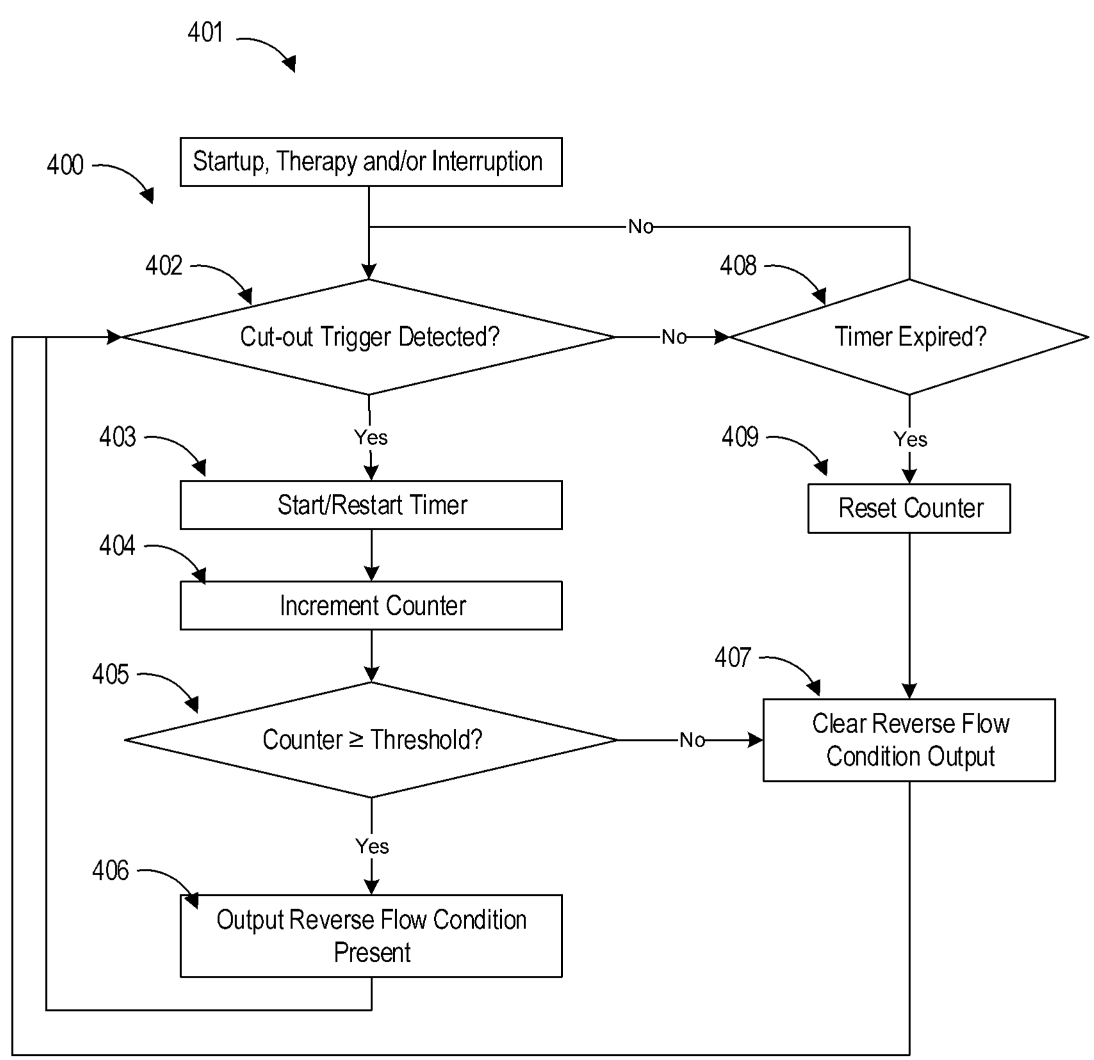
FIG. 4 illustrates an example method of detecting reverse flow involving a chamber outlet cut-out feature.

A detection of this pattern can be used to output a reverse flow condition being present, such as shown in the process 400 in FIG. 4. The process 400 can be implemented at the start-up of the humidifier and/or during therapy operation when the humidification system is providing respiratory therapy and/or by interrupting therapy operation 401. A controller of the humidification system disclosed herein can act as a reverse flow detector by performing the active detection process. The humidifier and/or the gases source can include the reverse flow detector.

At decision step 402, the controller can determine whether a trigger event has been detected. In this example, the trigger event can be the chamber outlet temperature reaching the first threshold temperature 306 of FIG. 3 (that is, the chamber outlet cut-out temperature), which can be higher than the chamber outlet set point.

If a trigger event is detected (that is, decision step 402 is satisfied), the controller moves to step 403. At step 403, the controller can start or restart a timer. The timer may be a pre-determined time interval. The controller can start or restart the timer, starting from the time that the trigger event was most recently detected. The timer can be restarted if it has already been started in response to the trigger event being detected at decision step 402 in a previous iteration of the process 400. The timer may be between about 5 and 120 minutes, or between about 5 and 60 minutes, or between about 5 and 30 minutes, or between about 5 and 20 minutes, or between about 5 and 10 minutes (including the two end values of the range). The controller then proceeds to step 404 where a counter is incremented by 1 or any other suitable value in response to the trigger event being detected. The counter can be equal to, or be indicative of, the number of trigger events that have been detected.

The controller then proceeds to decision step 405. At decision step 405, the controller can determine whether the counter is greater than or equal to a counter threshold. The counter threshold may be an integer. The counter threshold may be between 3 and 20, or between 5 and 15, or between 5 and 10 (including the two ends of the range). If the counter threshold is exceeded (that is, decision step 405 is satisfied, which indicates that the desired pattern is detected), then the controller can output the presence of a reverse flow condition at step 406. The output of a reverse flow condition being present can lead to the disabling of power to the heater plate 308 (see FIG. 3) and/or inspiratory conduit heat source 310 (see FIG. 3). Additionally and/or alternatively, the output of a reverse flow condition being present can lead to any one of the following non-limiting examples: producing an audio and/or visual alarm, changing a state of the controller, setting/resetting a flag, and/or acting as an input or "gateway" to another reverse flow detection method. If the counter threshold is not exceeded (that is decision step 405 is not satisfied and the desired pattern not being detected), then the controller proceeds to step 407 which clears any existing output of a reverse flow condition. If there is no existing output of a reverse flow condition, then the reverse flow condition remains cleared. The controller can then return to decision step 402.

If a trigger event is not detected (that is, decision step 402 is not satisfied), the controller can proceed to decision step 408. At decision step 408, the controller determines whether the timer, which was started or restarted at step 403 from a most recent trigger, has expired or elapsed. If the timer has not been started, that is, no triggering event has been detected in previous iterations of the process 400, the controller can return to decision step 402. If the timer has not expired (that is decision step 408 is not satisfied), then the controller can return to decision step 402. If the timer has expired (that is decision step 408 is satisfied), then the controller can proceed to step 409. At step 409, the controller can reset the counter. For example, the counter can be reset to a value of zero. The controller then proceeds to step 407.

The processes involving the chamber outlet cut-out feature can be configured for use in an invasive therapy mode or a high flow therapy mode. The processes can also be configured for use in any therapy modes, such as non-invasive therapy. Other parameters may be changed depending on the therapy mode, such as patient end setpoint, for example.

In other examples, the detectable pattern which correlates with an indication of a reverse flow condition may be based upon a periodicity of trigger events. In one example, the absolute difference of the time period between consecutive triggers can be calculated and compared. For example, a first time period difference can be calculated between a first and a second trigger, a second time period difference can be calculated between the second and a third trigger, and so on. If the difference, for example, absolute difference, is less than a threshold, then the controller can output a reverse flow condition. The output of a reverse flow condition may be further dependent on a predetermined number of consecutive absolute time differences being below the threshold, and/or a predetermined proportion of consecutive absolute time differences being below the threshold. In another example, the periodicity can be determined using an auto-correlation technique. In yet another example, the periodicity can be determined using a Fast Fourier Transform (FFT) technique. In yet another example, the periodicity can be determined from statistical techniques, such as comparing an interquartile range, variance, or standard deviation of the absolute difference between consecutive triggers with predetermined thresholds. In yet another example, the controller can use a sliding window for calculating the differences of the time period between consecutive triggers.

Example Active Detection Processes Using Temperature-Related Differential

Active detection processes can be implemented to detect a reverse flow condition. The active detection process can be implemented at the start-up of the humidifier and/or during therapy operation, when the humidification system is providing respiratory therapy. A controller of the humidification system disclosed herein can act as a reverse flow detector by performing the active detection process. The humidifier and/or the gases source can include the reverse flow detector.

Figure 5A:
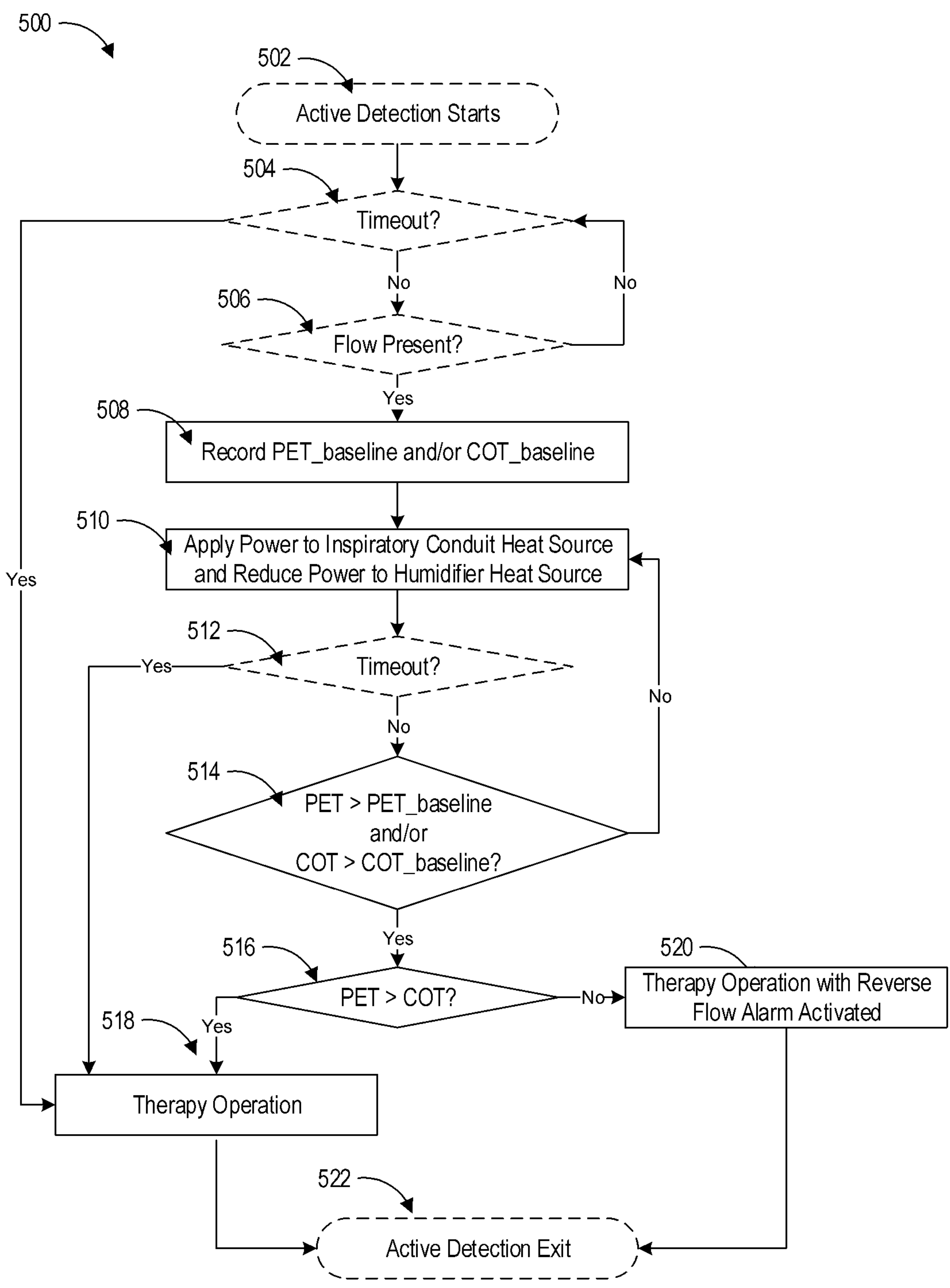
FIGS. 5A and 5B illustrate example active reverse flow detection processes.

As shown in FIG. 5A, an example active process 500 can begin at step 502, which can optionally include the controller powering on the humidifier if the process 500 is performed at start-up of the humidifier. If implementing the active process 500 during therapy operation, the controller can interrupt a therapy that is running in the humidification system. At step 502, the controller can disable power to the heater plate and the inspiratory conduit heat source or reduced the power to a level that can improve the stability when recording the baseline patient end and/or chamber outlet temperature values at step 508 (described in greater detail below). Alternatively, the controller can implement the active process 500 concurrently during therapy operation. In the concurrent implementation example, the controller can perform step 510 (described in greater detail below) on top of supplying the power to the inspiratory conduit heat source and/or the heater wire necessary for carrying out the therapy operation, and measure a corresponding change in the patient end and/or chamber outlet temperatures.

Optionally, at step 504, the controller can execute a first timeout reset function. If the method has not been started (or if the patient end temperature is greater than a certain limit, or otherwise) at the end of the first timeout reset function, the controller can exit the process 500 by entering (or resuming) therapy operation at step 518. The timeout function can prevent the controller from getting stuck in the process 500. If the process 500 has been started (or if the patient end temperature is under the certain limit, or otherwise) before the end of the first timeout function, the controller can proceed to decision step 506. At decision step 506, the controller can determine if a gases flow is detected. For example, the controller can determine that the gases flow is absent or too low to provide effective therapy if one or more sensors in the system detects a flow rate (which can be a filtered flow rate) at less than about 3 L/min or any other minimum flow rate, for example, continuously for a predetermined amount of time. The criteria for determining presence of flow can vary. If flow is not present (that is, decision step 506 is not satisfied), the controller can return to decision step 504 to execute the first timeout reset function again.

If flow is present (that is, decision step 506 is satisfied), at step 508, the controller can record the patient end temperature ("PET"-measured, for example, at the patient end of the inspiratory conduit) and/or the chamber outlet temperature ("COT") as baseline values ("PET_baseline", "COT_baseline" respectively). The baseline value may be an instantaneous temperature value of the PET and/or COT or an average value of the PET and/or COT calculated over a time window of temperature values. The baseline value can also be an average of the PET and the COT values or the PET_baseline and the COT_baseline values or any combination of the above, either instantaneously or over a window of time. Further, the baselines may be calculated using filtered values of the PET and/or COT. The respective temperature values can be provided by temperature sensors located at or near the patient end of the inspiratory conduit and the outlet of the humidification chamber, respectively. The controller may record one of the baseline patient end temperature or the baseline chamber outlet temperature. The controller can also record both the baseline patient end temperature and the baseline chamber outlet temperature to reduce false positives.

The controller can then proceed to step 510. At step 510, the controller can apply electrical power to the inspiratory conduit heat source and reduce (or disable) power to the humidifier heater plate. For example, the power applied to the inspiratory conduit and the humidifier heat sources can be in the form of a duty cycle. At Step 510, the controller can apply a 100% or substantially 100% duty cycle to the inspiratory conduit heat source. At step 510, the controller can apply a duty cycle in the range of about 0% to about 20% to the humidifier heat source. The controller can receive readings from the temperature sensors for the current patient end and chamber outlet temperatures.

The controller can continue to apply power to inspiratory conduit heat source until the current patient end temperature is greater than the baseline patient end temperature and/or the current outlet temperature is greater than the baseline outlet temperature, which can be implemented at decision step 514. At decision step 512, the controller can optionally execute a second timeout reset function, which can ensure that the process 500 limits the amount of time that the controller applies power to the inspiratory conduit heat source and/or humidifier heater plate at step 510, to prevent potential harm to the user of the humidification system, such as due to higher surface temperature and/or enthalpy to the user than when the system is in therapy operation. If the second timeout timer has expired, the controller can exit the process 500 by entering (or resuming) therapy operation at step 518.

If the second timeout timer has not expired, the controller can proceed to decision step 514. At decision step 514, the controller can compare the current patient end and/or chamber outlet temperatures with the respective baseline temperatures. Optionally, the controller can compare the current patient end and/or chamber outlet temperatures with the sum of the respective baseline temperatures and a respective offset. For example, the current patient end temperature can be compared with the combination of the baseline patient end temperature and an offset, and/or the current chamber outlet temperature can be compared with the combination of the baseline chamber outlet temperature and an offset. The offsets for the patient end temperature and the chamber outlet temperature can have the same value or different values. The offsets can ensure that enough heating has been provided to the inspiratory conduit heat source so that there is a more detectable separation between the patient end and chamber outlet temperatures, therefore further reducing the likelihood of false positives. The offset values can be up to about 5° C., or between about 1.5° C. and about 5° C., or about 2° C. If the current patient end and/or chamber outlet temperatures are not higher than the respective baseline temperatures (which can be with or without adding the respective offsets), the controller can go back to step 510 to apply electrical power to the inspiratory conduit heat source and reduce (or disable) power to the humidifier heat source.

If the current patient end and/or chamber outlet temperatures are higher than the respective baseline temperatures (which can be with or without adding the respective offsets), the controller can move to decision step 516. At decision step 516, the controller can compare the current patient end temperature with the current chamber outlet temperature. The patient end temperature is expected to be higher than the chamber outlet temperature in a normal flow condition because of the heating gradient in the inspiratory conduit. If there is a reverse flow condition, the unheated gases can enter the patient end of the inspiratory conduit and be heated as the gases reach the chamber outlet, resulting in a higher chamber outlet temperature than the patient end temperature. In some cases, the gases may be heated as a result of flowing through an expiratory conduit that has a heater wire, but the gases in and/or exiting the expiratory conduit may still be of a lower temperature than the chamber outlet temperature when flowing in a reverse flow condition.

Alternatively or additionally, the controller can compare different parameters that are related to the current patient end and chamber outlet temperatures at decision step 516. For example, the controller can compare a change in the current patient end temperature with a change in the current outlet temperature over a predetermined time period (for example, from every half a second to every two seconds, or about every second, or otherwise), and/or a rate of change in the current patient end temperature with a rate of change in the current outlet temperature over the predetermined time period (for example, from every half a second to every two seconds, or about every second, or otherwise).

Therefore, if the current patient end temperature (alternatively or additionally, the change in the current patient end temperature and/or the rate of change in the current patient end temperature) is greater than the chamber outlet temperature (alternatively or additionally, the change in the current chamber outlet temperature and/or the rate of change in the current chamber outlet temperature), which can be indicative of a normal flow condition, the controller can proceed to (or resume) its therapy operation at step 518. The controller can then exit 522 the process 500, which may finish the start-up process if the process 500 is running at startup. If the process 500 is performed at the start-up of the humidifier, before finishing the start-up, the controller can optionally test for a water-out condition for the liquid level in the humidification chamber. Performing the water-out test can be performed regardless of whether a reverse flow condition is detected. However, if a reverse flow condition is detected as mentioned above, it is preferred that the controller skips the water-out test.

The table below sets out various comparisons between PET and COT which may indicate a reverse flow. For example, if the chamber outlet temperature (alternatively or additionally, the change in the current chamber outlet temperature and/or the rate of change in the current chamber outlet temperature) is greater than the current patient end temperature (alternatively or additionally, the change in the current patient end temperature and/or the rate of change in the current patient end temperature), then this can be indicative of a reverse flow condition. In addition to any of the above, or as an alternative to, if the maximum rate of change in the current chamber outlet temperature is greater than the maximum rate of change in the current patient end temperature, then this can be indicative of a reverse flow condition. In addition to any of the above, or as an alternative to, if the rise time of the current chamber outlet temperature to a predetermined temperature is greater than the rise time of the predetermined current patient end temperature to a patient end predetermined temperature, then this can be indicative of a reverse flow condition. In some embodiments, where both POT and COT do not reach the associated predetermined temperature then the controller can revert to any one or more of the other comparisons. The controller can then activate a reverse flow alarm and proceed to (or resume) its therapy operation at step 520. Proceeding to therapy control can allow the controller to detect, for example, using the same process or a different process, whether a corrective action has been performed by a user, which can be a patient or a clinician, or others, to address the reverse flow alarm. The controller can then exit 522 the process 500 as described above.

Comparisons of PET with COT

| Comparison | PET comparison with COT indicating reverse flow |
|---|---|
| Rate of change | PET < COT |
| Change | PET < COT |
| Max rate of change | PET < COT |
| Temperature thresholds | PET < COT |
| Rise time (time of rise) | COT < PET |

Figure 5B:
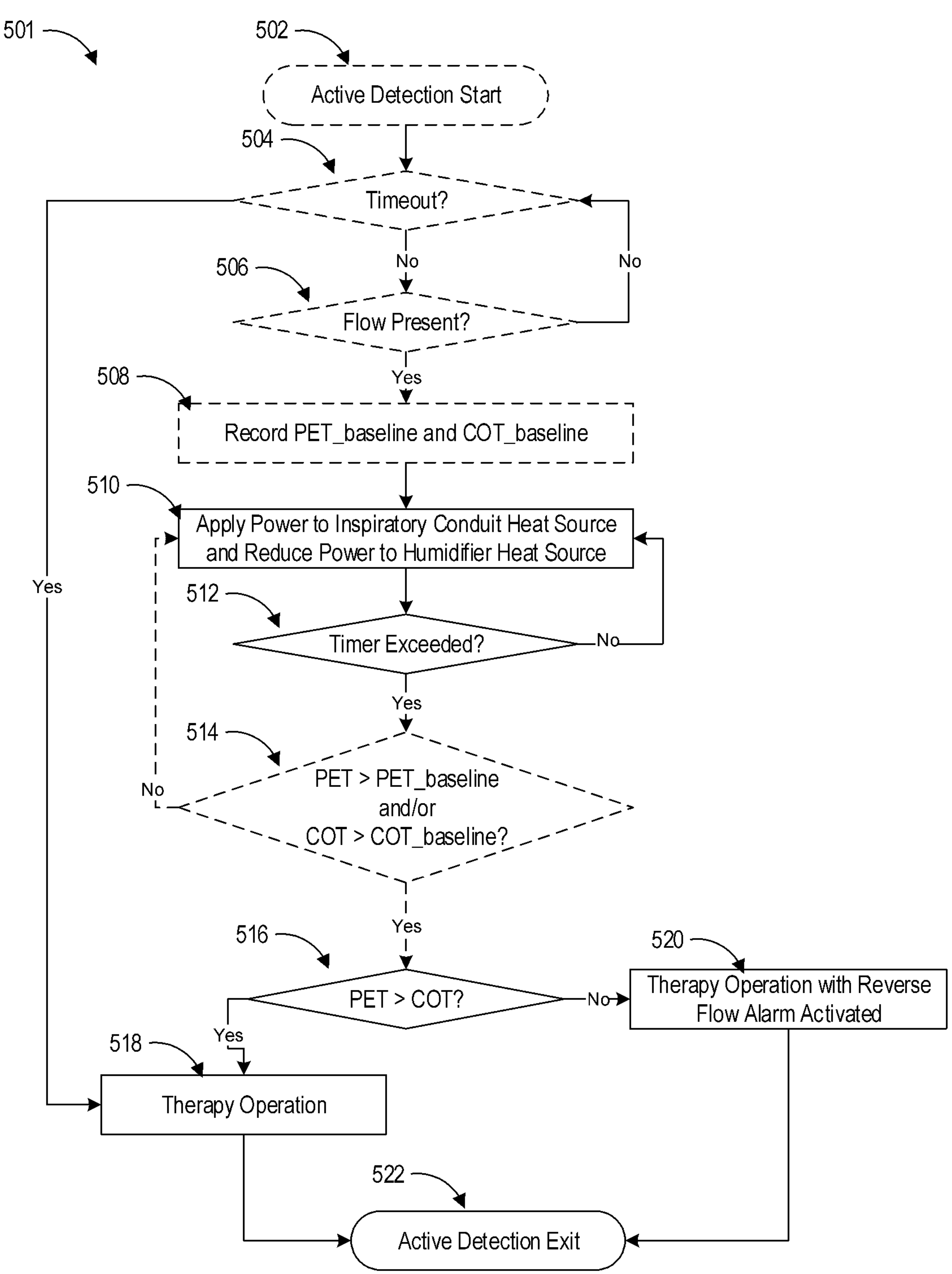

FIG. 5B illustrates an alternative active process 501 that can have any of the features of the process 500 in FIG. 5A except as described below. In the process 501 in FIG. 5B, the steps 508 and 514 are also optional and can be omitted. Instead, the step 512 is no longer optional and is performed so that the controller continues to apply electrical power to the inspiratory conduit heat source and reduce (or disable) power to the humidifier heat source for the duration of the timer at step 512. In some cases, the controller is configured to apply electrical power to the inspiratory conduit, for example by applying 100% duty cycle to the inspiratory conduit heat source, but ensuring that this does not exceed any pre-determined limits of the humidifier, such as a pre-determined surface temperature of the inspiratory conduit. The controller can assume that the duration of the timer would have allowed the current patient end and/or chamber outlet temperatures to be higher than the respective baseline temperatures (which can be with or without adding the respective offsets) so that the controller can optionally proceed directly to step 516.

Alternatively, at step 516, instead of, or in addition to, comparing PET and COT (as described in more detail above), reverse flow can be determined by measuring any one of (1) a value (for example an absolute value) of either or both of PET or COT; (2) a value (for example an absolute value) of either or both of PET or COT after a pre-determined period of time; (3) a rate of change of either or both of PET or COT; (4) a time to reach a predetermined value (for example a rise time) or rate of change of either or both of PET or COT, (5) a change of either or both of PET or COT over a predetermined period (in some cases this may be the same as the rate of change) or (6) a maximum rate of change of either or both of PET or COT. If the inspiratory tube is powered during a reverse flow condition, the temperature of the gases at the chamber outlet end (COT) will typically be higher than the temperature of the gases at the patient end (PET). Further, the temperature of the gases at the patient end (PET) would typically be changing less than the temperature of the gases at the chamber outlet end (COT). As a result, the change, rate of change and/or maximum rate of change of the temperature of the gases at the chamber outlet end (COT) will typically be greater than the change, rate of change and/or maximum rate of change of the temperature of the gases at the patient end. The rise time of the temperature of the gases at the chamber end, that is the time taken for the gases to reach a predetermined value (i.e. (4) as described above) may also be lower than rise time of the temperature of the gases at the patient end.

At step 516, a threshold can be applied to any or all of (1) a value (for example an absolute value) of either or both of PET or COT (for example as a as a patient end temperature threshold, or a second outlet temperature threshold); (2) a value (for example an absolute value) of either or both of PET or COT after a pre-determined period of time; (3) a rate of change of either or both of PET or COT (for example as a patient end temperature rate of change threshold, or an outlet temperature rate of change threshold); (4) a time to reach a predetermined value or rate of change of either or both of PET or COT, (5) a change of either or both of PET or COT over a predetermined period, or (6) a maximum rate of change of either or both of PET or COT. If one or more of the above parameters is lower than an associated threshold or is higher than an associated threshold, this can indicate a reverse flow condition. The table below sets out examples of comparisons of PET and COT to associated thresholds (for example as one or more COT or PET thresholds) which may indicate reverse flow. In some embodiments, to indicate reverse flow both the comparison of PET and COT and comparison of PET and/or COT to the thresholds below must indicate reverse flow for a reverse flow condition to be detected (for example activating a reverse flow alarm 520). Note that the opposite that is set out in the table may indicate a normal flow direction. In some embodiments, at least one of the POT and COT thresholds must indicate reverse flow for a reverse flow condition to be detected. The at least one of the POT and COT thresholds may relate to the same threshold (i.e. both COT and PET rate of change threshold comparisons indicate reverse flow) or different threshold (i.e. COT rate of change threshold and PET temperature threshold both indicate reverse flow). The threshold can be a function of any of flow rate, ambient temperature, therapy type, conduit type (for example adult or neonate), or expiratory heater wire power. For example, in cases where the expiratory heater wire is being powered, the temperature of the gases, when flowing in a reverse flow direction, will typically be higher than if the expiratory heater wire was not being powered. In such a case, the threshold can be increased, or the threshold can remain the same and the patient end temperature takes into account/adjusts for the additional heat provided by the expiratory heater wire. In another example, where PET is lower than a threshold and/or a rate of change of the patient end temperature is lower than a threshold, a reverse flow can be indicated. The thresholds as described above may be based on experimentally derived data, based on a particular system and/or a particular set of components.

Comparisons of PET to a threshold indicating reverse flow

| Threshold | PET comparison to threshold indicating reverse flow |
|---|---|
| Rate of change | lower than a threshold |
| Change | lower than a threshold |
| Max rate of change | lower than a threshold |
| Temperature value | lower than a threshold |
| Rise time (time of rise) | higher than a threshold |

| Comparisons of COT to a threshold indicating reverse flow | |
|---|---|
| Threshold | COT comparison to threshold indicating reverse flow |
| Rate of change | higher than a threshold |
| Change | higher than a threshold |
| Max rate of change | higher than a threshold |
| Temperature value | higher than a threshold |
| Rise time | lower than a threshold |

The active processes 500, 501 can advantageously result in a more easily detectable difference related to the patient end and chamber outlet temperatures because the inspiratory conduit heat source is driven to a higher heating capacity than during therapy operation of the humidifier.

During implementation of a reverse flow detection process, for example as described with respect to FIGS. 5A and 5B, one or more heating elements in the expiratory conduit can be provided with reduced energy or can be disabled. For example, during a start-up process of the humidifier, the heating elements in the expiratory conduit can be disabled as reverse flow detection implemented. In cases where the reverse flow detection algorithm is being implemented during therapy operation of the humidifier (for example, when delivering desired humidity to the patient), a cool down period (for example one or more heating elements in the expiratory conduit can be provided with reduced energy or can be disabled) can be implemented prior to commencing the reverse flow detection processes.

Example Passive Detection Processes Using System Parameters and/or Machine Learning Passive detection processes can be implemented to detect a reverse flow condition. A controller of the humidification system disclosed herein can act as a reverse flow detector by performing the passive detection process. Unlike the active processes described above, it is only necessary for the controller to receive sensor and/or device inputs for purposes of detecting a reverse flow condition. The humidifier and/or the gases source can include the reverse flow detector.

Figure 6:
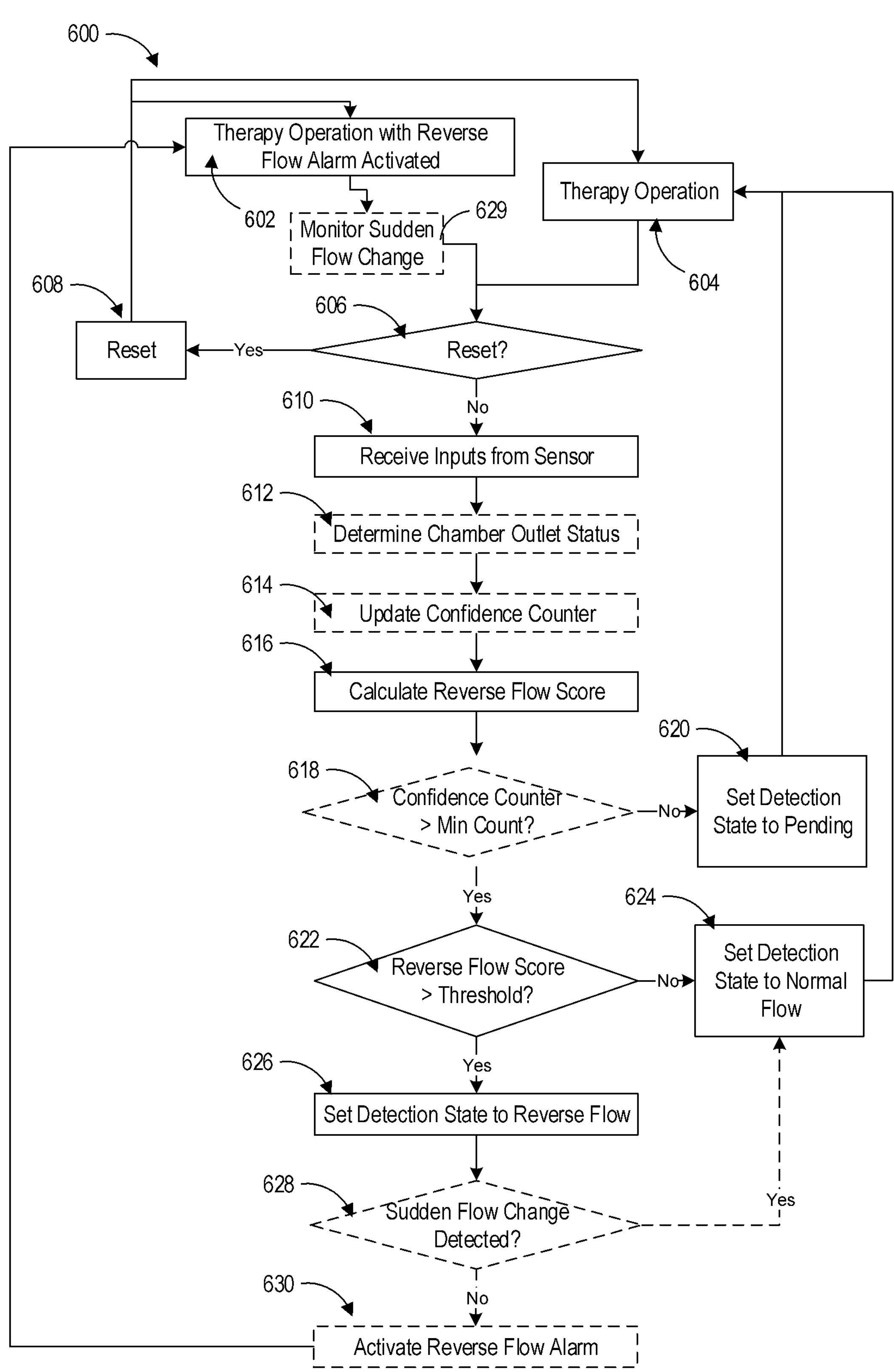
FIG. 6 illustrates an example passive reverse flow detection process.

The passive detection process can continue to run in the background during operation of the humidifier. The passive detection process may determine reverse flow based on one or more of: the inspiratory conduit ($T_{PE}$), a temperature of the humidifier inlet ($T_{CI}$), a temperature of the heater plate of the humidifier ($T_{HP}$), and/or a power of the heat source of the inspiratory conduit ($P_{HW}$). At the beginning of the process 600 as shown in FIG. 6, the controller can be in therapy operation 604, or therapy operation with a reverse flow alarm activated 602 if the process 600 has activated the reverse flow alarm in the previous loop. Optionally, the controller can monitor whether there is a sudden flow change. In a non-limiting example, as shown in FIG. 6, after step 602, the controller can monitor whether there is a sudden flow change at step 629. However, the controller can monitor whether there is a sudden flow change at any stage prior to decision step 628. The sudden flow change can be continuously monitored while the reverse flow alarm is active. The sudden flow change can be an indication of a corrective action (such as when the user has correctly connected the breathing circuit). The sudden flow change can be determined using a suitable flow sensor and/or temperature sensor. For example, the sensor/s may be an anemometer. A sudden flow change can be determined by any suitable methods, for example, by determining the percentage change in the flow rate over time or the absolute change in the flow rate over time. The values for the flow rate may be filtered. In a non-limiting example, a sudden flow rate change may be detected if the percentage change in flow rate is greater than about 40% over an about 30-second time period.

The controller can proceed to decision step 606 to determine whether the process 600 needs to be reset, that is, to loop back to step 602 or step 604. The controller can proceed to loop back to step 602 if the reverse flow alarm has been activated, otherwise it can loop back to step 604. The process 600 can be reset if certain system conditions are detected. Upon reset, the controller sets the detection state as pending, set a confidence counter to 0, and set certain other variables to default values. The pending state and the confidence counter will be explained in greater detail below.

A non-limiting example system condition includes the start-up test having not been finished. The passive detection process 600 can be implemented at the start-up of the humidifier and/or during therapy operation, when the humidification system is providing respiratory therapy. However, when the passive detection process 600 is run in the background during set-up, the passive detection process 600 can be reset at step 608 when the controller determines at step 606 that the set-up algorithm has not finished. Other example system conditions that cause the reset at step 608 of the passive detection process 600 can include certain components (for example, the inspiratory conduit or the sensor cartridge) not being connected, errors from sensors (for example, temperature sensors), just to name a few.

If no system conditions causing the reset have been met, at step 610, the controller can receive various inputs from the sensors, which can include, but are not limited to, temperature sensors at or near the humidifier inlet, the humidifier outlet, the heater plate of the humidifier, and/or a patient end of the inspiratory conduit.

Optionally at step 612, the controller can determine a humidification chamber outlet state. The determination can be based on whether a temperature at the humidifier outlet has reached a pre-set limit. The pre-set limit can be a chamber outlet cut-out temperature limit as described above. As will be described below, certain details of the subsequent steps of the process 600 can vary based on the determined humidification chamber outlet state.

Optionally, at step 614, the controller can determine whether the sensors inputs received at step 610 are at a steady state value (for example, for a predetermined amount of time) and update a confidence counter accordingly. The steady state is reached when a rate of change of the inputs is below a fluctuation limit for the predetermined amount of time. The controller can increase the confidence counter by one count if at least some of the sensor inputs received at step 614 are at a steady state value. This step can ensure that the sensor readings have sufficient stability before the readings are used for determining whether there is reverse flow. If the chamber outlet cut-out temperature limit has been reached as determined in step 612, the controller can ignore some of the sensor inputs, for example, the chamber outlet temperature sensor reading, when updating the confidence counter. The controller can still increment the confidence counter even if the ignored sensor inputs are not at steady state.

At step 616, the controller can calculate a reverse flow score. The calculation can be based on an equation obtained using learning software (for example, machine learning and/or the like). The calculation can also or alternatively be based on an equation obtained using experimental or observed data. The equation to determine a reverse flow score can generally include parameters such as a temperature at the patient end of the inspiratory conduit ($T_{PE}$), a temperature of the humidifier inlet ($T_{CI}$), a temperature of the heater plate of the humidifier ($T_{HP}$), and/or a power of the heat source of the inspiratory conduit ($P_{HW}$). For example, the system may detect a reverse flow condition where the reverse flow score is determined and compared to a threshold value.

As another example, the learning software can generate coefficients for the reverse flow score equation. If the chamber outlet cut-out temperature limit has been reached as determined in step 612, the controller can use the following formula:

$$\text{Reverse Flow Score}=a*T_{PE}+b*T_{CI}+c*T_{HP}+d*P_{HW}$$

If the chamber outlet cut-out temperature limit has not been reached as determined in step 612, the controller can use a different formula as shown below:

$$\text{Reverse Flow Score}=A*T_{PE}+B*T_{CI}+C*T_{HP}+D*P_{HW}$$

The various coefficients in the two formulas may or may not be the same.

The values inputted into the equations can include the raw values, or the raw values after they have been filtered, for example, low-pass filtered. Alternatively or additionally, the equation can include one or more of the following non-limiting example parameters: inspiratory conduit heat source power/voltage/current/resistance, heater plate power/temperature/voltage/current/resistance, patient end temperature, chamber outlet temperature, chamber inlet temperature, chamber inlet flow rate, chamber inlet power dissipation, chamber outlet flow rate, chamber outlet power dissipation, internal sensor cartridge (if present) temperature, and/or mains frequency.

The controller can optionally proceed to decision step 618 to determine whether the confidence counter has reached a minimum count. The step 616 and the decision step 618 can be performed in any order. If the minimum count has not been reached, the controller can set the detection state to pending at step 620 and repeat the process by returning to therapy operation at step 604 (or to the therapy operation with the reverse flow alarm activated step 602). The pending state indicates there is not enough confidence in the sensor readings to determine the direction of the flow. The confidence counter is not reset in the pending state and is allowed to accumulate as the process restarts at step 604 (or step 602) until there is enough confidence to proceed to analyze the reverse flow score to determine whether reverse flow has occurred. If the minimum count has been reached, the controller can proceed to decision step 622 to determine whether the reverse flow score calculated at step 616 has reached a threshold. The threshold can be 0, or any other suitable value.

If the reverse flow score is under the threshold, the controller can proceed to step 624 to set the detection state to normal flow, indicating that no reverse flow is detected. The controller can then proceed to therapy operation at step 604. If the reverse flow score has met or exceeded the threshold, the controller can set the detection state to reverse flow at step 626. At optional step 630, the controller can activate the reverse flow alarm before proceeding to step 602 to resume therapy control and to repeat the process 600.

Optionally, at decision step 628 after the detection state has been set to reverse flow, the controller can determine whether a sudden change in the gases flow has been detected from the monitoring of sudden change starting at step 629. If a sudden flow change is detected, the controller can proceed to step 624 by updating the detection state to normal flow. If a sudden flow change is not detected, the controller can proceed to step 630 or directly to step 602. Additionally or alternatively, the decision step 628 can be performed after the reverse flow alarm has been activated. If a sudden flow change is detected, the alarm can be deactivated.

The passive reverse flow detection processes described herein can be advantageous in that there is no interruption to providing the therapy to the user, making it more convenient to the user while still improving user safety by detecting the reverse flow conditions. Further, additional waiting time may not be required for the sensors to reach a steady state during therapy operation of the humidification system so that the passive processes can be implemented. In some cases, additional waiting time may be required for the sensors to reach a steady state during therapy operation of the humidification system so that the passive processes can be implemented.

Additionally, the passive detection processes can be used in combination with the active detection processes. For example, when the passive detection process has detected a reverse flow condition, the active process can be implemented to confirm the detection. As noted above, the active process may be able to detect the reverse flow condition with more certainty in some cases.

TERMINOLOGY

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain optional features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Any methods disclosed herein need not be performed in the order recited. The methods disclosed herein include certain actions taken by a practitioner; however, they can also include any third-party instruction of those actions, either expressly or by implication.

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on general purpose computer hardware, or combinations of both. Various illustrative components, blocks, and steps have been described above generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A reverse flow detector for a humidification system that includes a gases source, a humidifier, and a breathing circuit, and configured to detect a reverse flow condition in the humidification system, the reverse flow detector comprising:

a controller configured to:

receive a sensor signal indicative of an outlet temperature at an outlet of a chamber of the humidifier that carries humidification fluid; and in response to detecting at least two trigger events related to the outlet temperature of the chamber, output an indication of a reverse flow condition, wherein a first trigger event comprises the chamber outlet temperature reaching a first threshold temperature.

2. The reverse flow detector of claim 1, wherein the controller is configured to output the indication of the reverse flow condition further in response to detecting a pattern of the at least two trigger events.

3. The reverse flow detector of claim 1, wherein the controller is further configured to start or restart a timer in response to detecting a first one of the at least two trigger events.

4. The reverse flow detector of claim 3, wherein the controller is configured to restart the timer from a time when a trigger event was most recently detected.

5. The reverse flow detector of claim 3, wherein the controller is further configured to determine whether the timer has expired in response to no trigger event being detected.

6. The reverse flow detector of claim 1, wherein the controller is further configured to initiate a second method of detecting an indication of a reverse flow condition in response to outputting the indication of the reverse flow condition, and/or configured to be displayed on a user interface of the humidifier and/or the gases source.

7. The reverse flow detector of claim 1, wherein the controller is configured to output the indication of the reverse flow condition by activating an alarm, wherein the alarm is visual and/or audible.

8. The reverse flow detector of claim 7, wherein the alarm is activated only after a pre-determined operating time period has been reached.

9. The reverse flow detector of claim 1, wherein the first threshold temperature comprises a chamber outlet cut-out temperature.

10. The reverse flow detector of claim 1, wherein the first threshold temperature is one or more of above 37° C.; between 37.1° C. and 50° C.; between 38° C. and 45° C.; between 42° C. and 44° C.

11. The reverse flow detector of claim 1, wherein, in response to detecting a first one of the at least two trigger events, the controller is further configured to detect a subsequent one of the at least two trigger events only after the chamber outlet temperature has fallen below a second threshold temperature.

12. The reverse flow detector of claim 11, wherein the second threshold temperature is below the first threshold temperature and above a chamber outlet temperature set-point.

13. The reverse flow detector of claim 1, wherein the detecting is performed during setup of the humidification system or just after setup is finished.

14. The reverse flow detector of claim 1, wherein the detecting is performed during steady state operation of the humidification system or by interrupting steady state operation for a period of time.

15. The reverse flow detector of claim 2, wherein the controller is configured to detect the pattern based on a predetermined periodicity of the at least two trigger events.

16. A humidifier for a humidification system, wherein the humidifier comprises the reverse flow detector of claim 1.

17. The humidifier of claim 16, wherein the controller is further configured to disable power to a heater plate of the humidifier and/or a heat source in an inspiratory conduit of the breathing circuit in response to outputting the indication of the reverse flow condition.

18. The humidifier of claim 17, comprising a safety feature configured to disable power to the heater plate of the humidifier and/or the heat source in the inspiratory conduit in response to outputting the indication of the reverse flow condition.

19. The reverse flow detector of claim 1, wherein the controller is further configured to detect a subsequent trigger event of the at least two trigger events, wherein the subsequent trigger event comprises the chamber outlet temperature reaching a third threshold temperature.

20. The reverse flow detector of claim 19, wherein the first threshold temperature and the third threshold temperature are the same.

* * * * *